United States Patent [19]
Callstrom et al.

[11] Patent Number: 5,691,154
[45] Date of Patent: Nov. 25, 1997

[54] ENZYME LINKED IMMUNOASSAY WITH STABILIZED POLYMER SACCHARIDE ENZYME CONJUGATES

[75] Inventors: Matthew R. Callstrom, Columbus, Ohio; Mark D. Bednarski, Berkeley, Calif.; Patrick R. Gruber, St. Paul, Minn.

[73] Assignee: Cargill, Incorporated, Minneapolis, Minn.

[21] Appl. No.: 469,662

[22] Filed: Jun. 6, 1995

Related U.S. Application Data

[60] Division of Ser. No. 791,915, Nov. 13, 1991, Pat. No. 5,492,821, which is a continuation-in-part of Ser. No. 613,224, Nov. 14, 1990, abandoned.

[51] Int. Cl.$^6$ ............ G01N 33/53; C12N 11/06; C12N 11/08; C12N 9/96; C12N 9/00
[52] U.S. Cl. ............ 435/7.6; 435/180; 435/181; 435/182; 435/183; 435/188; 530/200; 530/201; 530/202; 530/203; 530/204; 530/205; 530/206; 530/207
[58] Field of Search ............ 530/200–207; 435/180–183, 187, 7.6

[56] References Cited

U.S. PATENT DOCUMENTS

| | | | |
|---|---|---|---|
| 3,625,827 | 12/1971 | Wildi et al. | 435/175 |
| 3,806,417 | 4/1974 | Beaucamp et al. | 527/201 |
| 4,038,140 | 7/1977 | Jaworek et al. | 527/201 |
| 4,081,329 | 3/1978 | Jaworek et al. | 527/200 |
| 4,119,589 | 10/1978 | Horn et al. | 527/203 |
| 4,182,695 | 1/1980 | Horn et al. | 527/203 |
| 4,652,524 | 3/1987 | Modrovich et al. | 435/188 |
| 4,673,707 | 6/1987 | Tsai et al. | 527/207 |
| 4,711,840 | 12/1987 | Nowinski et al. | 527/202 |
| 4,845,035 | 7/1989 | Fanta | 435/148 |
| 5,041,292 | 8/1991 | Feijen | 424/484 |

FOREIGN PATENT DOCUMENTS

| | | |
|---|---|---|
| 161188 | 11/1985 | European Pat. Off. |
| 450628 | 10/1991 | European Pat. Off. |
| 2019502 | 7/1970 | France |
| 2600897 | 1/1988 | France |
| 57-202309 | 12/1982 | Japan |
| 8909624 | 10/1989 | WIPO |
| 9005534 | 5/1990 | WIPO |

OTHER PUBLICATIONS

Stryer, "Biochemistry," (1988), Freeman Co., N.Y., pp. 302–303.

*Biotechnology Letters*, Vol. 6, No. 12, issued 1964; K. Takahashi et al., "Polyethylene Glycol–Modified Enzymes Trap Water On Their Surface and Exert Enzymic Activity in Organic Solvents," pp. 765–770.

*Die Angewandte Makromolekulare Chemie*, Vol. 76/77, issued 1979, U. Seitz et al., "Neu Reaktive Mikrogele als Trager fur Enzyme," pp. 319–327.

*Trends in Biochem. Sci.*, vol. 3, issued 1978, J.J. Marshall, "Manipulation of the Properties of Enzymes by Covalent Attachment of Carbohydrate," pp. 79–83.

*Cell Surface Carb. and Biol. Recogn.*, issued 1978, G.R. Gray et al., "Proteins Containing Reductively Aminated Disaccharides: Chemical and Immunochemical Characterization," pp. 583–594.

*Trends in Biochemical Tech.*, Vol. 9, No. 11, issued Nov. 1991, B. Mattiasson et al., "Tailoring the Microenvironment of Enzymes in Water–Poor Systems," pp. 394–398.

K. Takemoto et al., "Functional Monomers and Polymers, Procedures, Synthesis, Applications, "published 1987 by Marcel Dekker (N.Y.), pp. 461–503.

*Makromol. Chem.*, vol. 188, issued 1987, J. Klein, "Synthesis of Some Poly (Vinylsaccharide)s of the Amide Type and Investigation of Their Properties," pp. 1217–1232.

*J. Polymer Sci.*, PART A-1, Vol. 6, issued 1968, Y. Iwakura et al., "Preparation of Polymers Containing Sugar Residues," pp. 1625–1632.

*Enzyme Microb. Technol.*, vol. 13, issued Jul. 1991, H. Kise et al., "Immobilization of Proteases to Porous Chitosan Beads and Their Catalysis for Ester and Peptide Synthesis in Organic Solvents," pp. 584–588.

*Enzyme Microb. Technol.*, vol. 14, issued Feb. 1992, S.A. Khan et al., "Polyethylene Glycol–Modified Subtilisin Forms Microparticulate Suspensions in Organic Solvents," pp. 96–100.

*Enzyme Microb. Technol.*, vol. 14, issued Feb. 1992, H.F. Gaertner et al., "Increased Activity and Stability of Poly-(Ethylene Glycol) –Modified Trypsin," pp. 150–155.

*J. Am. Chem. Soc.*, vol. 114, issued Jan. 1992, P. Wang et al., "New Carbohydrate–Based Materials for the Stabilization of Proteins," pp. 378–380.

(List continued on next page.)

*Primary Examiner*—David M. Naff
*Assistant Examiner*—Jon P. Weber
*Attorney, Agent, or Firm*—Fitch, Even, Tabin & Flannery

[57] ABSTRACT

An improvement in enzyme linked immunoassays is disclosed wherein the enzyme is in the form of a water soluble polymer saccharide conjugate which is stable in hostile environments. The conjugate comprises the enzyme which is linked to the polymer at multiple points through saccharide linker groups.

16 Claims, 11 Drawing Sheets

OTHER PUBLICATIONS

*Chem Eng. News*, issued 13 Jan. 1992, S. Borman, "Immobilized Enzymes Act in Organic Solvents," pp. 5–6.

*Makromol. Chem. Rapid Commun.*, vol. 6, issued 1985, J. Klein et al., "Emulsion Polymerization of Poly (Meth–acryloylglucose)," pp. 675–678.

*Makromol. Chem. Rapid Commun.* vol. 7, issued 1986, A. Kobayashi et al. "Enhanced Adhesion and Survival Efficiency of Liver Cells in Culture Dishes Coated with a Lactose–Carrying Styrene Homopolymer," pp. 645–650.

O'Neil et al., *Biotechnol. and Bioeng.*, XIII, 319–322 (1971).

Patel et al., *Biopolymers*, 5, 577–582 (1967).

Patel et al, *Biopolymers*, 5, 583–584 (1967).

Robinson et al., *Biochim. Biophys. Acta*, 242, 659–661 (1971).

Weibel et al, *Biochem. J.*, 125, 801–807 (1971).

Yakunitskaya et al., *Preparation of Conjugates of Subtilisin BPN' and Dextrans*, 174–178 (1980).

Axen et al., *Biopolymers*, 9, 401–413 (1970).

Barker et al., *Carbohyd. Res.*, 20, 1–7 (1971).

Davey et al., *Enzyme Microb. Technol.*, 11, 657–661, (1989).

Fisher et al, *Macrolide Antibiotics* 553–606 (1984).

Kilbanov, *Chemtech*, 354–359 (1986).

Luthra et al., *J. Chem. Soc. Perkin Trans. II.*, 1575–1578 (1987).

Manecke et al. *Reactive Polymers*, 3, 251–260 (1985).

Mitz et al., *Nature*, 169, 576–577 (1961).

Mozhaev et al., *Enzyme Microb. Technol.*, 6, 50–59 (1984).

Russell et al., *J. Biol. Chem.*, 263, 11624–11626 (1988).

Russell et al., *Biochem. Soc. Trans.*, 17, 1145, (1989).

Suen et al., *Makromol. Chem.*, 186, 255–260 (1985).

Torchilin et al., *Biochimica et Biophysica Acta*, 522, 277–283 (1978).

Wong et al., *J. Am. Chem. Soc.*, 945–953 112, (1990).

Wykes et al., *Biochim. Biophys. Acta*, 250, 522–529 (1971).

Zaks et al., *Proc. Natl. Acad. Sci., USA*, 82, 3192–3196 (1985).

Zaks et al., *Science*, 224, 1249–1251 (1984).

Bird et al., *Chemistry and Industry*, 1331–1332 (1960).

Black et al., *J. Chem. Soc.*, 4433–4439 (1963).

Black et al., *Chemistry and Industry*, 1624 (1962).

Haworth et al., *J. Chem. Soc.*, 488–491 (1946).

Imoto et al., *Institute of Polytechnics*, 210–211 (1962).

Kimura et al., *Institute of Polytechnics*, 232–236 (1962).

Kimura et al., *Institute of Polytechnics*, 155–160 (1961).

Klein et al., *Makromol. Chem., Rapid Communication*, 7, 621–625 (1986).

Nichols, Jr. et al., *J. Am. Chem. Soc.*, 2020–2022 (1946).

Nichols, Jr. et al., *J. Am. Chem. Soc.*, 46–49 (1945).

Nichols, Jr. et al., *J. Am. Chem. Soc.*, 1625–1627 (1944).

Otey et al., *Ind. Eng. Chem. Prod. Res. Develop.*, 11, 70–73 (1972).

Overberger et al., *J. of Pol. Sci.* 7, 1011–1022, (1969).

Treadway et al., *J. Am. Chem. Soc.*, 1038–1039 (1945).

Whistler et al., *J. Org. Chem.*, 2961–2962 (1962).

Barbas et al., *J. Am. Chem. Soc.* 110, 5162–5166 (1988).

Jakubke et al., *Angew. Chem. Int. Ed. Engl.* 24, 85–93 (1985).

Kasche, *Proteolytic Enzymes*, 125–143 (1989).

Kitaguchi et al., *J. Am. Chem. Soc.*, 111, 9272–9273 (1989).

Kuhl et al., *Tetrahedron Let. 21*, 893–896 (1980).

Luthi et al., *J. Am. Chem. Soc.*, 106, 7285–7286 (1984).

Margolin et al., *J. Am. Chem. Soc.*, 109, 3802–3804 (1987).

Margolin et al., *J. Am. Chem. Soc.*, 109, 7885–7885 (1987).

Morihara et al., *Biochem. J.*, 163, 531–542 (1977).

Pugh, "Enzymes as Catalysts in Organic Synthesis," 217–232 (1986).

West et al., *J. Chem. Soc., Chem. Commun.*, 417–418 (1986).

Gray, "Preparation of Antigens," 155–160.

Lonngren et al., "Preparation of Antigens," 160–162.

Smith et al., "Preparation of Antigens," 169–171.

Zopf et al., "Preparation of Antigens," 163–169.

Zopf et al., "Preparation of Antigens," 171–175.

Cramer, *Methods in Carbohydrate Chemistry*, 1, 242–246 (1962).

Mrozik et al., *J. Med. Chem.*, 25, 658–663 (1982).

Richardson, *Methods in Carbohydrate Chemistry* 6, 218–224 (1972).

Zaborsky, "Immobilized Enzymes", 49–60, 149–165 (1973).

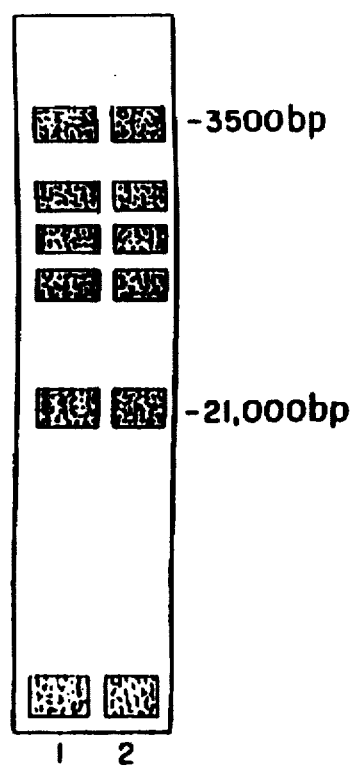
FIG. 14  AGAROSE GEL PBR 322
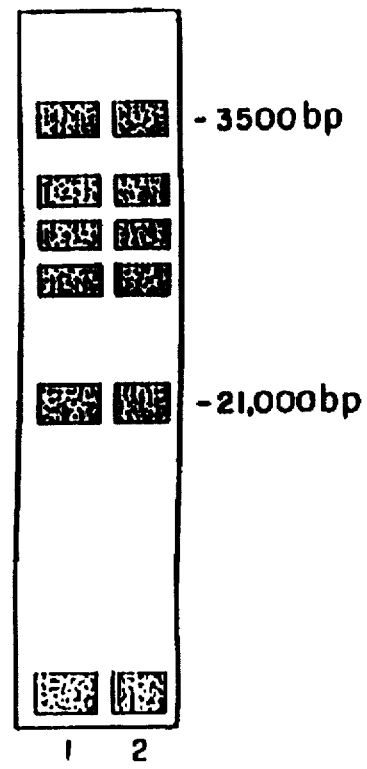
FIG. 15  AGAROSE GEL LAMBDA-DNA
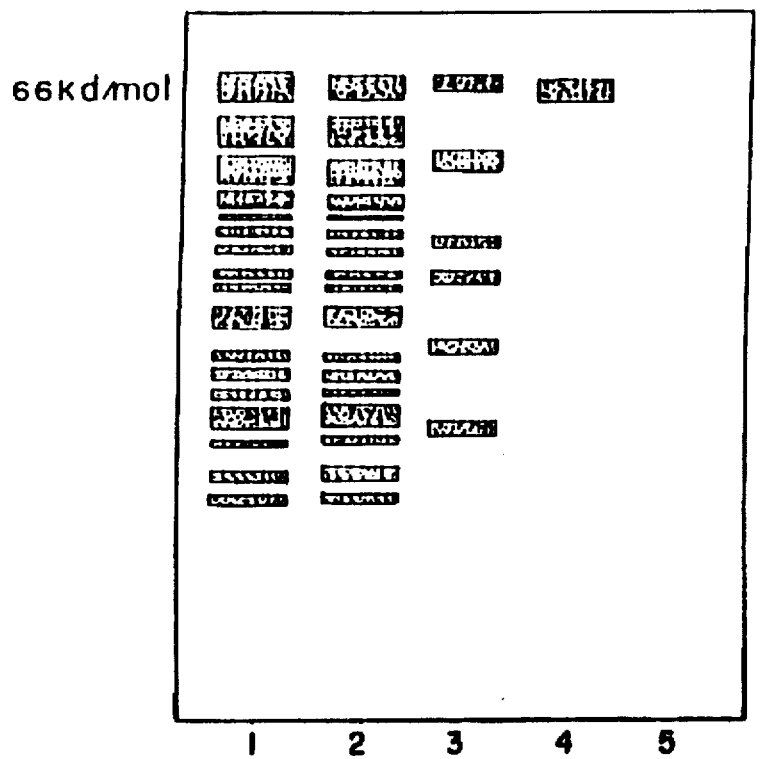
FIG. 16  SDS-PAGE ic
ENZYME LINKED IMMUNOASSAY WITH STABILIZED POLYMER SACCHARIDE ENZYME CONJUGATES This application is a division of application Ser. No. 07/791,915, filed Nov. 13, 1991 and issued as U.S. Pat. No. 5,492,821, which is a continuation-in-part application of Ser. No. 07/613,224, filed Nov. 14, 1990, now abandoned.

The research related to this application was supplied under several arrangements, one which was contract DE-AC03-76SF00098 between the U.S. Department of Energy and the University of California for the operation of Lawrence Berkeley Laboratory. In relation to the contract, the U.S. Government has certain interests in the invention.

BACKGROUND OF THE INVENTION

FIELD OF THE INVENTION

This invention herein relates to polymer protein compounds or protein polymer conjugates, a method of making such compounds and a method of stabilizing proteins in the form of the polymer protein conjugates of the invention in a hostile environment.

Proteins are used in a variety of applications. Whether the proteins, such as enzymes, antibodies, and the like, are used in diagnostics, the food industry, the bioconversion of organic compounds in either water or organic solutions etc., a common problem with using proteins in all of these applications is the instability of the protein itself. Enzymes, antibodies, and the like would be more useful if they were stable in a soluble or an insoluble form at elevated temperatures, in non-optimal aqueous solutions or in organic solutions while retaining the ability to recognize and bind molecules, and in some cases, exhibit catalytic activity. The protection of proteins against proteolytic attack is also highly desirable.

Proteins including enzymes are quite sensitive to their environment. Such environmental conditions include the pH of the solution, temperature, shear forces, the presence of organic solvents, buffer conditions, reactions with irreversible and reversible inhibitors, proteolysis of the enzyme by proteins in the solution, adhesion to other proteins or to the wall of the vessel. The stability of a protein is in reference to its conformational stability and biological activity. The effect of temperature, organic solvent, pH, and storage on the stability of the protein is largely determined by the conformational stability of the protein. Inactivation of the protein is primarily due to denaturation of the protein; however, changes in the protein (such as chemical modification) can also occur, resulting in inactivation without denaturation of the protein. When conditions are not optimal, the protein may be partially or fully denatured which results in a decrease or loss of activity.

It is highly desirable to stabilize proteins and their activity because of their potential uses in organic synthesis and diagnostics in the pharmaceutical and agricultural industries. Available methods, however, do not provide a general approach to solving the problem of protein stability. Moreover, the majority of these methods are not applicable where it is advantageous to use the protein or enzyme either in solution or in an insoluble form.

Inactivation and denaturation is of particular concern in the diagnostics field, because the use of proteins such as labile enzymes and antibodies can result in unreliable test results and limited shelf life of a test kit product. Furthermore, the methods of controlling the denaturation of proteins are expensive and burdensome. The effect of immobilization on the stability of enzymes is highly variable. The immobilization can give enzymes that have enhanced, diminished, or unchanged activity relative to the native enzymes. Examples of each effect exist (For a review of the effect of immobilization on the stability of enzymes, see: Zaborsky Immobilized Enzymes CRC Press: Boca Raton at 49-165 (1978)). For example, one possible way to stabilize the structure and reactivity of a protein such as an enzyme is by immobilization on a soluble or insoluble support. In addition to the possible stabilization of the protein, immobilization on insoluble supports is desirable because of the ease of recovery of the protein and the prevalent use of equipment for applications which use insoluble material.

Advantages of immobilization of proteins on a soluble support include higher rates of transfer of substrate to the protein and greater accessibility of the substrates to the protein. Another advantage to the use of a soluble support is that the solubility of the system allows the use of reactor configurations such as ultrafiltration reactors or membrane reactors and use in diagnostic assays where soluble proteins may be necessary. The inconvenience of proteins immobilized on solid supports may also cause problems in assays where optical and electrical measurements are being taken.

Prior to the invention, difficulties associated with the immobilization of proteins including enzymes using known methodologies include: necessary prior activation of the polymeric support, relatively harsh chemical treatments, which destroy or reduce the activity of the protein, necessary for the immobilization process, and the number of functional groups, or the density of functional groups available for the attachment on the polymeric support. The methods do not offer a general solution to the stabilization and immobilization of protein structure.

Moreover, when enzymes and antibodies are used in applications such as an enzyme-linked immunosorbent assay (ELISA), the problem prior to the invention herein was a lack of stability (because of the pH of the solution, temperature, shear forces, the presence of organic solvents, the lack of buffer, reaction with irreversible inhibitors, proteolysis of the antibody and enzyme by proteinases in the solution, and the like) of both the enzymes and the antibodies used. In addition, the sensitivity of the enzymes to organic solutions made the tests limited to aqueous solutions.

Therefore, it is an object of the invention to provide stabilized proteins through polymer protein compounds.

Another object of this invention is to provide a method for stabilizing a protein in an environment which would reduce an intended functional property of the protein.

Still another object of this invention is to provide a method for making the polymer protein compounds of the invention.

Another object of the invention is to provide for a method of synthesizing peptides.

Still another object of the invention is to provide for a method of assaying using the polymer protein compounds of the invention.

These and other objects and advantages of the invention will be found by reference to the following description.

SUMMARY OF THE INVENTION

The invention herein includes a method of stabilizing proteins, is a polymer protein compound and a method for making the polymer protein compounds of the invention.

The invention also includes the use of the stabilized protein in assays and provides a method of synthesizing peptide bonds.

According to the invention, the protein is stabilized by covalently bonding it to a particular polymer structure which includes hydroxyl groups in an amount effective for stabilizing the protein. In one aspect of the invention, the hydroxyl groups and polymer cooperate with other polar groups such as polar groups in the region of the protein to provide the stabilization of the protein. When the polymer is covalently bonded to the protein according to the invention, the polymer protein compound of the invention provides stabilization to the structure of the protein which is part of the compound of the invention. These stabilized proteins retain their functional and catalytic activity in environments where a similar non-stabilized protein would lose or have a reduced functionality and catalytic activity.

In order to achieve protein stabilization, there are three primary portions of the composition of the invention regardless of the route of synthesis. These portions of composition are: a protein, a linker group, and a polymer. The protein is bonded to the linker group which in turn is bonded to the polymer. The polymer and/or linker provide hydroxyl groups in an amount effective for stabilizing the protein, as aforesaid.

The polymer must have or permit substitution to provide for one or more pendent groups extending from and along the main chain which pendent groups will be reactive with other compounds to form a linker group or which pendent group itself will form a linker group which will bond the protein to the polymer through the linker group. In an important aspect of the invention the polymer is selected from the group consisting of a polyvinyl polymer, an acrylic polymer, a polyester polymer, a polyamide polymer and mixtures thereof. The polymer has a main chain which has the pendant groups. These pendant groups may form part or all of the linker group. The linker group is covalently bonded to the polymer main chain through an ester, amide, ether, thioether, thioester, peptide or a carbon-carbon linkage. The linker group is covalently bonded to the protein (using methods mild enough that the catalytic and functional activity of the protein is not destroyed) through ester, amide, ether, thioether, thioester, or amine linkages. Generally, the linker group can be derived from linkers which are carbohydrates or polyols. The carbohydrate portion of a glycoprotein may be a linker and be bonded directly to the polymer pendant group which is reactive with the glycoprotein.

The proteins can be enzymes, antibodies, and the like. Forming the protein to linker bond (if the linker is already on the polymer) or the linker to polymer bond (if the protein is already bonded to the linker) or polymerization bonds (if the protein and linker are already attached to a polymerizable group) is done under sufficiently mild conditions so that the catalytic and functional activity of the protein is not destroyed.

In order to achieve the polymer-linker group-protein compositions, a linker can be incorporated into a monomer which then is polymerized, which polymer is subsequently bonded to the protein; the linker may be bonded to a polymer, with the polymer-linker combination subsequently being bonded to the protein; the linker may be bonded to the protein and the protein-linker combination may be subsequently bonded to the polymer; a linker with a polymerizable group may be bonded to a protein and subsequently polymerized to a protein-linker-polymer.

According to the method of the invention, an intended functional property of the protein is stabilized such that the functional property is either maintained to be at least equal to the native protein (the protein in its natural state) or it is enhanced over a reduced activity that the protein would have in a hostile environment such as elevated heat, adverse aqueous or organic solvents, proteolytic attack or pH other than the normal environment of the native protein.

The linker group includes all of the atoms between the polymer main chain (which is made of the atoms bonded to each other-to form the length and longitudinal axis of the polymer) and the amino acid residue of the protein attached to the linker and will separate the main chain of the polymer from the protein by two or more carbon atoms and include at least three hydroxyl groups. In a very important aspect of the invention the linker group will be a saccharide group which includes the residue of a monosaccharide, a disaccharide and a trisaccharide.

An important aspect of the invention are compounds which have specific linker polymer combinations. Specifically an important aspect of the invention is where the polymer is an acrylic polymer combined with a saccharide linker which forms a linker group which links the protein to the acrylic polymer. In this aspect of the invention, the acrylic polymer has a molecular weight of at least 500, preferably at least about 5,000 and most preferably 300,000 or greater.

Another important aspect of the invention includes polymer protein compounds whereby solubility of the compounds in aqueous and organic solvents can be controlled by cross-linking the polymer protein compounds and by polymerizing the compounds of the invention into gels. In this aspect of the invention the polymer protein compound of the invention can be made insoluble which will permit the composition of the invention to be utilized in currently known processing equipment.

The polymer protein compound or conjugated protein is stable and can be employed under adverse conditions which are hostile to the protein and would reduce an intended functional property of the protein. As a result, an important aspect of the invention is that new and improved methods for assaying using the compounds. of invention are provided. Thus, the invention herein could be used in a wide variety of industrial, pharmaceutical and diagnostic processes that utilize enzymes, antibodies, and the like in solution, in suspension, and immobilized on surfaces.

BRIEF DESCRIPTION OF THE DRAWINGS

FIG. 14 illustrates the cleavage patterns of λ DNA digested by conjugated EcoR1 in lane 2 and native EcoR1 in lane 1.

FIG. 15 illustrates the cleavage patterns of PBR322 plasmid digested by the conjugated EcoR1 and native EcoR121.

FIG. 16 illustrates the digestion of bovine serum albumin by conjugated trypsin in lane 1 and native trypsin in lane 2. Note that lanes 3, 4 and 5 are molecular weight markers.

DETAILED DESCRIPTION OF THE INVENTION

Figure 1:
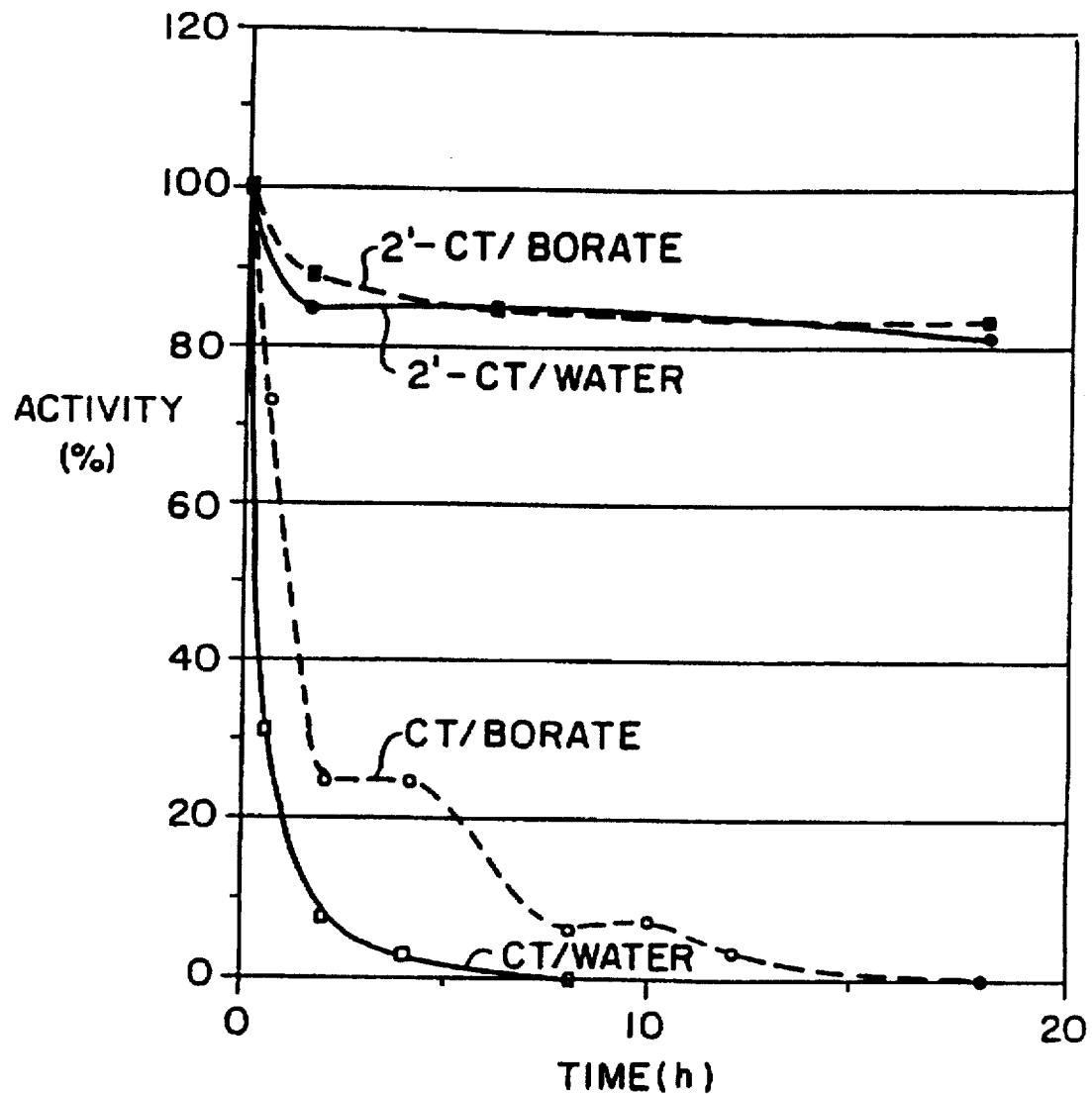
FIG. 1 describes the stability of the poly(2-N-methacrylamido-2-deoxy-D-glucose)-chymotrypsin conjugate and native chymotrypsin in buffer and water at 45° C.

Enzymes, antibodies, and the like are complex proteins each with a specific sequence of amino acids. The structure of the protein is critical to the activity of the protein such as the catalytic activity of an enzyme and the capacity of an antibody to recognize ligands.

The method and compounds of the invention described herein provide a means for stabilizing proteins by protecting or maintaining the structure of the protein by using effective amounts of hydroxyl groups, the structure of a polymer, and in some instances polar groups covalently bonded in the compounds of the invention for stabilizing the proteins in a particular polymeric composition. According to the invention, proteins are stabilized such that if put into a hostile environment, intended function is maintained to be at least equal to the proteins in their natural states or is enhanced over a reduced activity that the proteins would have in the hostile environment.

"Acrylic polymer" means a polymer or copolymers of

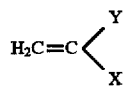

wherein
y=alkyl having 1 to 4 carbon atoms or H;

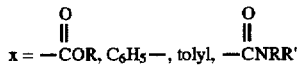

R=straight chain or branched alkyls having 1 to 12 carbons,

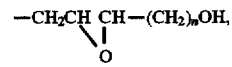

H,

2-hydroxy ethyl, 3-chloro-2-hydroxypropyl, 2-hydroxy-1-methylethyl, 2-hydroxypropyl, 3-hydroxypropyl, 2,3-dihydroxypropyl, 2-hydroxybutyl, 4-hydroxybutyl, diethylene-glycol, 5-hydroxypentyl, 6-hydroxyhexyl, triethyleneglycol, 7-hydroxyheptyl, 3,4-dihydroxybutyl, 5-hydroxypentyl, 6-hydroxyhexyl, 1,3-dimethyl-3-hydroxybutyl, 5,6-dihydroxyhexyl, 7-hydroxyheptyl, a residue of a mono-, di-, and trisaccharide, such as 2-deoxy-D-glucose;
R'=H
n=2 to 7.

"Polyester" or "polyester polymer" means the polymerized reaction product of polyacids and polyols; polyacids include diacids such as isophthalic, terephthalic, and fumaric acids and $HOOC(CH_2)_nCOOH$ where n=2 or more and "dimer acids", anhydrides of diacids such as maleic, phthalic, hexahydrophthalic, and succinic, and anhydrides of polyacids such as trimellitic acid anhydride. The diacids or polyols, however, must have or permit substitution to provide for one or more pendent groups along the main chain which will be reactive with other compounds to form a linker group or which pendent group itself will form a linker group which will bond the protein to the polymer through the linker group. In the case of a polyester, hydroxyl group or ester groups may be such pendent groups extending from the main chain of the polyester. The polyols which react to form the main chain of the polyester include linear diols such as $HO(CH_2)_m OH$ where m=2 or more, branched aliphatic diols such as neopentyl glycol, 1,3-butylene glycol, propylene glycol and 1,3-dihydroxy-2,2,4-trimethylpentane, cycloaliphatic diols such as hydroquinone, 1,4-dihydroxymethyl-cyclohexane and "hydrogenated bisphenol A", diol ethers such as diethylene glycol, triethylene glycol and dipropylene glycol, and polyols such as glycerol, pentaerythritol, trimethylol propane, trimethylol ethane, dipentaerythritol, sorbitol and styrene-allyl alcohol copolymers.

"Polyamide" or "polyamide polymer" means a polymer in which the structural units are linked by an amide or thioamide groupings such as the reaction product of a diamine and dibasic acid.

"Polyvinyl polymer" means polymers polymerizable through a vinyl group of the monomer.

In this application, the polymers have a molecular weight of at least about 500, preferably at least about 5,000 and most preferably at least about 300,000. It is believed that molecular weights of the polymers may go as high as 100,000,000 or more.

"Protein" means proteins, including proteins modified to include additional amino groups such as lysine groups, polypeptides, enzymes, antibodies, and the like, which are composed of a specific sequence of amino acids.

"Polar group" means any group which has an affinity for or an ability to bind with water, such as

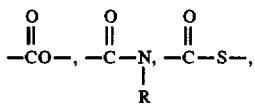

as defined infra as A and B.

"Hostile environment" means an environment which will reduce a functional property or activity of a protein over a native protein or that which the protein has in its natural state. A hostile environment can include temperatures which create adverse thermal environments which could be elevated or reduced temperatures, solvents such as an organic solvent, the presence of proteases, pH and lack of buffer.

THE COMPOUNDS OF THE INVENTION

The compounds of the invention comprise a protein covalently bonded to a polymer through a linker group. The protein of the compounds is stabilized so that under hostile conditions an intended functional property of the protein is either maintained to be at least equal to the native protein or it is enhanced over a reduced activity that the protein would have in hostile conditions by providing an environment which includes hydroxyl groups in the region where the polymer, linker group and protein are covalently bonded. The hydroxyl groups may be on the polymer or on the linker group and are in an effective amount and close enough to the covalently bonded combination of the polymer, linker group and protein to stabilize the protein as described. In one aspect of the invention, the hydroxyl groups and polymer cooperate with other polar groups such as polar groups in the region of the protein to provide the stabilization of the protein. Generally, however, the linker group will have hydroxyl groups, and as such, in a preferred aspect of the invention, will be a polyol, a carbohydrate or carbohydrate-like.

In one aspect of the invention the polymer is selected from the group consisting of a polyvinyl polymer, an acrylic polymer, a polyester polymer, a polyamide polymer and mixtures thereof. The polymer has a main chain which has pendent groups. These pendent groups may form part or all of the linker group. The main chain and/or the pendent group include hydroxyl groups which stabilize the protein. The linker group is covalently bonded to the polymer main chain through an ester, amide, ether, thioether, thioester, peptide (one or more amide linkages), or a carbon to carbon linkage. If the pendent group on the polymer forms all of the linker group, the pendent group should be reactive such that it will covalently bond to the protein. If the pendent group on the polymer main chain forms part of the linker group between the polymer main chain and the protein, it should be reactive with a linker to permit covalent bonding between the pendent group and the linker. After bonding with the protein, the linker group is completed.

The linker group is covalently bonded to the protein through an ester, amide, ether, thioether, thioester, peptide (one or more amide linkages) or amine linkage. Generally this is synthetically achieved by using methods mild enough that the catalytic and functional activity of the protein is not destroyed.

The linker group includes all atoms between the polymer main chain and the amino acid residue of the protein attached to the linker group and will separate the main chain of the polymer from the protein by two or more carbon atoms and have at least three hydroxyl groups. As used herein, a linker is a precursor to a linker group. In a very important aspect of the invention the linker group is a saccharide group which includes the residue of a monosaccharide, a disaccharide and a trisaccharide. A linker group which includes hydroxyl groups stabilizes the protein; and while there is not necessarily a defined limited as to the exact number of carbon atoms in a linker group, steric and kinetic considerations limit the size of the linker group to a total of about 60 carbon atoms.

The polymer, linker group and protein can be attached to one another, such as shown below:

wherein

Polymer=main chain of a polymer selected from the group consisting of a polyvinyl polymer, a polyacrylic polymer, a polyester polymer and a polyamide polymer, Protein=residue of a protein, wherein

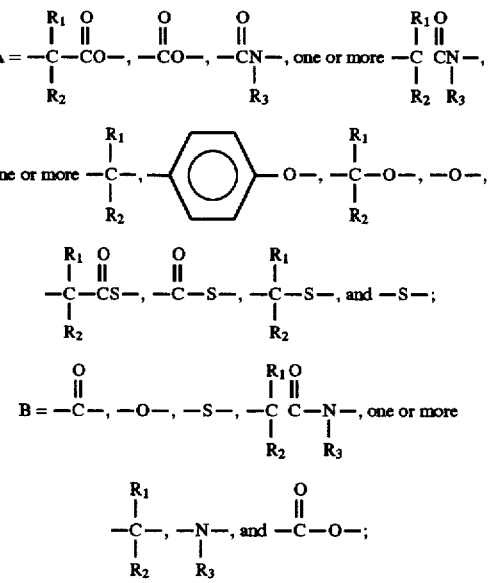

$R_1$ and $R_2$=H, OH, acetoxy, alkoxy, phenylene and all of the substituents defined for R in the definition of acrylic polymer, halogen and phosphate;

$R_3$=all of the substituents defined for R in the definition of acrylic polymer;

L=

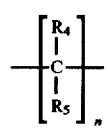

having at least three hydroxyl groups
n=at least 2, and
$R_4$ and $R_5$=H, OH, alkoxy,

and hydrocarbon which may have one or more hydroxyl groups, ether linkages or ester linkages, and $R_6$ being hydrocarbon which may have 1 or more hydroxyl groups, 1 or more ether linkages and L not more than 60 carbon atoms, or L=a saccharide group which includes the residue of a mono-, di- or trisaccharide. Preferably $R_1$, $R_2$, $R_4$ and $R_5$ are selected from the group consisting of H, OH and alkyl having 1 to 4 carbons. Preferably $R_3$=H. The polymer is covalently bound to and substituted with at least about 1 weight percent of the linker groups.

The protein will be bonded to the polymer linker group combination at least at one point on the protein, however, stabilization of the protein will be increased as the number of bonding points between the protein with a linker polymer combination increases. Further, there may be more than one protein bonded to one polymer and one protein may be bonded to more than one polymer to create a matrix of polymer chains which are linked by covalent bonds.

Where the protein is to be bonded to a linker, as at B, the protein has functional groups, which on interaction with the linker, will provide the residue B when subjected to an appropriate reaction with the linker. Where a linker which includes a saccharide is used, proteins that have pendant amino functionality are preferred, such as those proteins which contain lysine and arginine groups. Preferably, the protein contains more than one functionality such as a ε-lysine residue for attachment to the linker and preferably, the protein does not contain ε-lysine residues in the active site. However, it is possible to block coupling of lysines in the active site by adding a reversible inhibitor to the reaction solution for the reductive amination reaction or for reaction with a lactone based pendent group. Most preferably, the protein contains at least one lysine residue and preferably greater than 3 surface lysine residues. The pendant amino functionality on the protein readily attaches a saccharide linker which is in turn attached to the polymer. In this aspect of the invention, the linker group can include a saccharide based compound which will have aldehyde or lactone functionality capable of forming covalent bonds with the amino functionality of the protein molecule. This pendant aldehyde or lactone functionality on the saccharide may be protected as hereafter described. An advantage of the invention is that in connection with the saccharide linker when there is an aldehyde precursor, the linked protein may be protonated at the nitrogen of the protein (which nitrogen is incorporated into B) at a pH similar to the pH of the protein. This protonation is not permitted with the lactone precursor.

In an important aspect of the invention which includes an acrylic polymer, the compounds of the invention have the following Formula III:

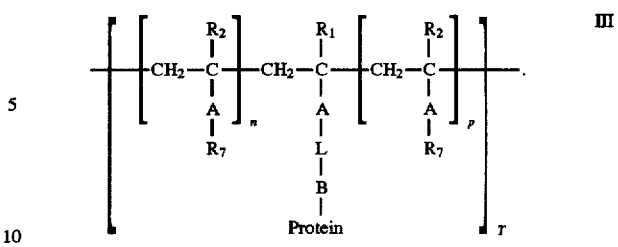

wherein:

$R_1$ and $R_2$ are independently alkyls having 1 to 4 carbons or H group;

Where $R_7$=all of the substituents defined for R in the definition of acrylic polymer; wherein A is defined above, B is defined above, L is defined above.

p=0 to 50,000;

n=0 to 50,000; and

T=10 to 50,000; the total repeating units represented by p, n and T is not more than 50,000.

The protein is bonded to the polymer by at least one covalent bond, but may be covalently bonded at multiple points along the protein. Moreover, the above formula does not necessarily represent a protein as being repeated in the parenthesis, but more than one protein may be represented by the above formula as being bonded to the same polymer. Further, the protein can be linked or bonded to another polymer chain to provide cross-linking of the compounds of the invention through a protein, as will be more fully described infra.

A particularly important aspect of the invention is where the polymer is an acrylic polymer and where the linker group includes residues of monosaccharides, disaccharides or trisaccharides, or derivatives thereof, and mixtures thereof. Preferably, these linkers are residues of monosaccharides or derivatives thereof. The monosaccharides are preferably 2-amino-2-deoxy-D-glucose, 3-amino-3-deoxy-D-glucose, or 6-amino-6-deoxy-D-glucose. The linker is most preferably 6-amino-6-deoxy-D-glucose.

The molecular weight of the polymers that can be used for the formation of polymer protein compounds is broad, at least 500 to 100,000,000 or more. Oligomeric materials where the degree of polymerization is low, i.e. T in Formula III=about 10, can provide stabilization to the protein. However, it is desirable to use polymers with high molecular weights in order to be able to use the conjugate in a membrane enclosure with large pores to allow rapid diffusion of substrates to the protein. It is also desirable to use a high molecular weight polymer so that the conjugate can be separated from reactants and products by filtration with a membrane, or in the case of the use of insoluble conjugates, to use a filter to effect the separation. The polydispersity of the polymer materials is not critical, although it is highly desirable to have a polydispersity of less than 5 in order to minimize the loss of low molecular weight material when a large pore membrane is used. It is most desirable to use materials with polydispersities of less than 1.5.

The polymer III may be prepared solely (p=0) from individual monomer units which may incorporate a saccharide linker group with a pendant protected aldehyde or lactone functionality. The polymer may also be in the form of either random, regular, or block copolymers. For example, the copolymerization of 18 with methacrylamide (19) gives (20).

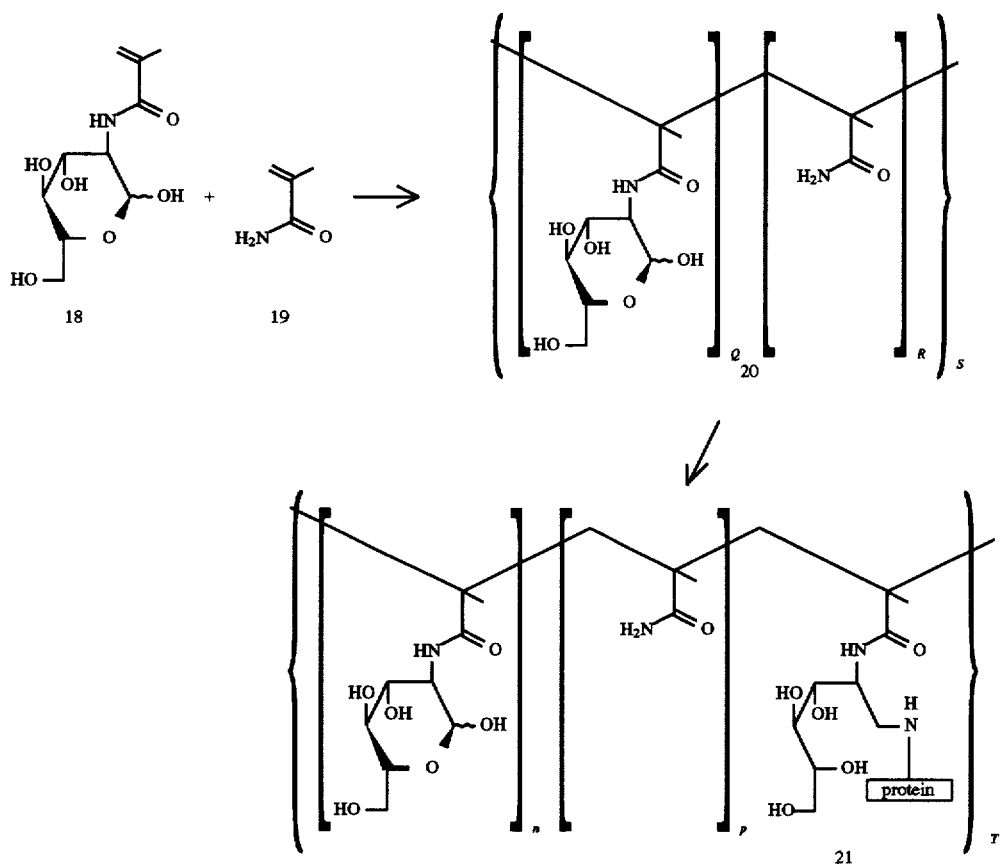

The values for n, p, and T are quite variable, ranging from n and Q=0–50,000; p and R=0–50,000; T and Q=10–50,000. It is most desirable to have the value of T to be as high as possible containing many segments of the monomer encompassed by n. The polymers can be block, random, or homopolymers although a random or homopolymer is desirable, a homopolymer is the most desirable. A polymer with n values of 1–100 and p values of 1–5 and the total molecular weight greater than 500,000 is highly desirable. The most desirable polymer is where n greater than 1,000 and p=0. Where an acrylic polymer is used, it is, of course, possible to use comonomers other than methacrylamide in this invention. In particular, a comonomer which is another saccharide-derived monomer is highly desirable. Reaction of (20) with a protein gives (21) where the protein surface ε-lysine resides react with aldehyde functionality contained in (20). As described above, the linker (20) and (21) could also be in the form of a di- or trisaccharide, or could be a five-membered ring or a six-membered ring joined to a five-membered ring.

The monomer or polymerizable group as defined in the polymer above in Formula III, the group in the parentheses with the repeating integer n is used to form the polymer chain above or along with the comonomer if so desired. The monomer group can be monomers which provide the acrylic polymer as defined above.

Comonomer units having the formula

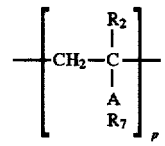

may be used to form the polymer chain include heterogeneous mixtures of two or more monomers defined above.

The Saccharide Linker Group

A very important aspect of the invention is where a protein is an enzyme or antibody, or a mixture of enzymes and antibodies, especially when linked to the polymer through a residue which includes a saccharide. Enzymes which may be used in the invention include enzymes used in bioprocessing industries, in medical tests and in quick tests for toxins. Enzymes important to the invention include but are not limited to transferases such as cycloglucanotransferases (CGTase); proteases such as metalprotease, Staph V8 protease, rennet, papain, subtilisin, ficin, rennin, pronase E, bromelain and [neutral] proteases such as pepsin; oxgenases such as lipooxygenase; hydrolases such as lipass, [phospho]-lipase, cellulase hemicellulase, α-glucanase, β-glucanase, trypsin, pectinase, cellobiohydrolase, [alpha-beta-]-[gluco-galacto-]-sidases, transglucosidase, pullanase, cellobiase, [dextran-levan] sucrases; isomerases such as xylose isomerase and glucose isomerase; amylases such as alpha amylase, beta amylase, fungal alpha amylase and glucoamylase; oxidases such as glucose oxidase, glucose (1,2)-oxidase, peroxidase, catalase and horseradish peroxidase; esterases such as cholestrol esterase, phytase and pectinmethyl esterase.

In this aspect of the invention, the linker group may be a saccharide which may have six or five membered rings as shown in formulas I or II below. The six-membered ring is selected from the group consisting of Formulas Ia, Ib, Ic, and Id each of which is shown below. The five-membered ring saccharide is selected from the group consisting of Formulas IIa, IIb, IIc and IId each of which are shown below. A and B are shown in the formulas below to show how the saccharide ring(s) are bonded to the polymer through A and the protein through B.

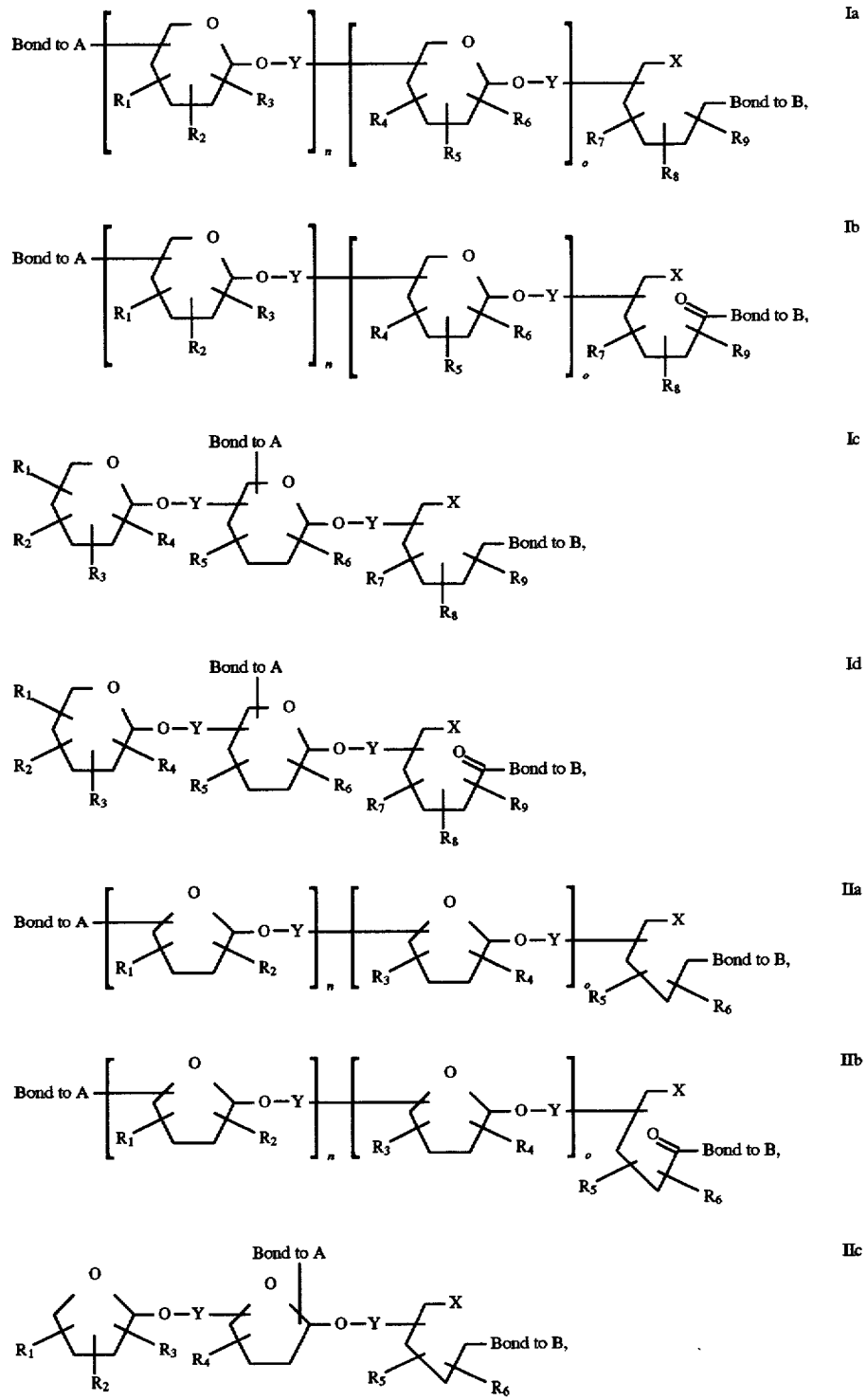

and

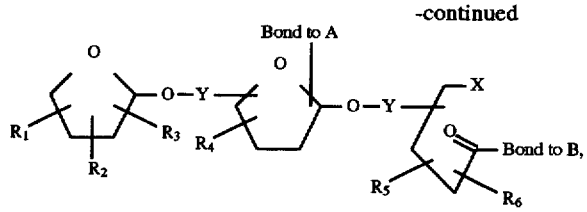

wherein
n=0 or 1;
O=0 or 1;
Y=bond or —CH$_2$—;
A as defined above;
B as defined above; and
R$_1$ through R$_9$ selected from the group consisting of H, OH, alkoxy, acetoxy, all of the substituents defined for R in the definition of acrylic polymer, halogen and phosphate.

Preferably R$_1$ through R$_9$ are H, OH, or an alkyl having 1 to 4 carbon atoms.

As shown in either case of a five or six membered saccharide ring, the polymer can be bound to the second sugar in the disaccharide or the third saccharide ring from the ring bonded to the protein. Further, although not shown in the above formulas, five and six membered rings may be bonded together to form one saccharide linker group.

Making The Compounds Of The Invention

The polymer protein compound of the invention can be prepared in several ways. In general, the polymer protein compound of the invention may be made by bonding a polymer or monomer without linker to a separate linker with the linker being bonded to the protein. In one aspect of making the compounds of the invention, the polymer monomer or the polymer portion of the compounds of the invention is the residue of a monomer or polymer having a pendant group with a functional group reactive with a functional group on the linker. In one aspect of the invention, the polymer portion of the compound of the invention is the residue of a polymer selected from the group consisting of a polyvinyl polymer, an acrylic polymer, a polyester polymer and a polyamide polymer. The linker also includes a second functional group which is reactive with the protein. The functional group on the protein which is reactive with the linker preferably is an amine group.

In one aspect of the synthesis of the compounds of the invention, monomer units which incorporate the linker are made. Thereafter the polymer which includes the linker is made by polymerizing the monomer units which include the linker making the linker available for bonding to the protein. After that polymerization, the polymer with the linker extending therefrom is reacted with a protein or mixture of proteins to link the protein to the polymer through the linker to form the polymer protein compound of the invention.

To form the individual monomer-linker unit used herein, a linker and monomer group are joined to give the A position respectively of the formula above. In an aspect of this invention, the monomer-linker units contain linkers that are derivatives of glucose and galactose. The monomer-linker units can be, but are not limited to 2-N-methacrylamido-2-deoxy-D-glucose, 3-N-methacrylamido-3-deoxy-1,2;5,6-diisopropylidine-D-glucose, 3-N-methacrylamido-3-deoxy-D-glucose, 6-N-methacrylamido-6-deoxy-D-glucose, 6-O-methacryloyl-D-glucose, 6-O-vinyl-1,2;5,6-diisopropylidene-D-galactose and 2-N-methacrylamido-2-deoxy-D-glucose-6-phosphate. In this aspect of the invention, most preferably, the individual monomer-linker units are 2-N-methacrylamido-2-deoxy-D-glucose, 3-N-methacrylamido-3-deoxy-3-D-glucose or methacrylamido-6-deoxy-D-glucose.

A monomer-linker unit suitable for the purposes of the invention described herein can be prepared by treatment of 2-amino-2-deoxy-D-glucose hydrochloride, which is commercially available from chemical suppliers such as Aldrich Chemical Co., with one mole equivalent of methacryloyl chloride and two equivalents of sodium methoxide in methanol at about 25° C. to give 2-N-methacrylamido-2-deoxy-D-glucose.

A monomer-linker unit can be prepared by treatment of a glucose derivative such as 3-amino-3-deoxy-D-glucose with 1 mole equivalent of methacryloyl chloride and 1 mole equivalent of a base such as sodium methoxide at about 0° C. to about 60° C. in a solvent such as methanol, to give 3-N-methacrylamido-3-deoxy-D-glucose where A is equal to —CONH—. The 3-amino-3-deoxy-D-glucose can be prepared by treatment of 3-amino-3-deoxy-1,2:5,6-di-O-isopropylidene-D-glucofuranose with about 1N acid, such as hydrochloric acid, in water for about 4 hours at about 25° C. The 3-amino-1,2:5,6-di-O-isopropylidene-D-glucofuranose can be prepared by the reduction of 3-azido-3-deoxy-1,2:5,6-di-O-isopropylidene-D-glucofuranose (prepared by the method described by Richardson. 6 *Methods in Carbohydrate Chemistry* at 218–224 (1972) with ammonium carbonate and platinum oxide.

A monomer-linker unit can be prepared by treatment of 3-amino-3-deoxy-1,2:5,6-di-O-isopropylidene-D-glucofuranose with 1 mole equivalent of methacryloyl chloride and 1 mole equivalent of a base such as sodium methoxide at about 0° C. to about 60° C. in a solvent such as methanol, to give 3-N-methacrylamido-3-deoxy-1,2:5,6-di-O-isopropylidene-D-glucofuranose where A is equal to —CONH—.

Additionally, a monomer can be attached to the linker at the 6-position by treatment of a glucose derivative such as 6-amino-6-deoxy-D-glucose with 1 mole equivalent of methacryloyl chloride and 1 mole equivalent of a base such as sodium methoxide at about 0° C. to about 60° C. in a solvent such as methanol, to give 6-N-methacrylamido-6-deoxy-D-glucose where A is equal to —CONH—. The 6-amino-6-deoxy-D-glucose can be prepared by treatment of 6-amino-1,2-O-isopropylidene-D-glucofuranose with about 1N acid, such as hydrochloric acid, in water for about 4 hours at about 25° C. The 6-amino-1,2-O-isopropylidene-D-glucofuranose can be prepared by the method described by Cramer. 1 *Methods in Carbohydrate Chemistry* at 242–246 (1962).

A monomer-linker unit can be formed by treating 2-amino-2-deoxy-D-glucose with hexokinase and then treating with an equivalent of methacryloyl chloride and two equivalents of sodium methoxide in methanol at about 25° C. gives 2-N-methacrylamido-2-deoxy-D-glucose 6-phosphate. Adenosine triphosphate, formed by pyruvate kinase phosphorylation of adenosine diphosphate with phosphoenol pyruvate serves as the source of phosphate for hexokinase.

When a di- or trisaccharide is used as the linker, the individual linker unit is prepared as described for the preparation of the monosaccharide linker units. The maltose or maltotriose linker is joined to the monomer with methacryloyl anhydride in a solvent such as pyridine or triethylamine to form the monomer-linker unit. The amount of methacryloyl anhydride used is about 1 mole equivalent to about 2 mole equivalents based on the linker.

To form the polymer, when the linker portion of the monomer-linker unit is water-soluble, polymerization is carried out using a free-radical initiator such as ammonium persulfate or 2,2'-azobis(2-amidinopropane) hydrochloride in water. The polymerization is conducted at 0° C. to about 100° C., preferably at 0° to about 70° C.

When the linker portion of the monomer-linker unit is organic-soluble, polymerization may be carried out in water using a free-radical initiator, but the reaction could also contain an emulsifier. The free-radical initiator could include azobis(isobutyronitrile) or benzoyl peroxide and the like. Solution polymerization may be carried out using free-radical initiator such as azobis(isobutyronitrile) or benzoyl peroxide in solvents such as benzene, acetonitrile, hexane, diethyl ether and the like. The amount of initiator is used in an amount of about 0.5 to about 20 mole % based on the linker. Preferably, the initiator is used in an amount of about 1.0 to about 5.0 mole %. The emulsifying agent used herein could be Triton X-405 or Triton X-100, which can be purchased from Rohm and Haas. The emulsifier is used in an amount of about 5 to about 20 weight percent based on the weight of monomer-linker unit. The polymerization is conducted at about 0° to about 100° C., preferably at about 25° to about 70° C.

Important polymers of the previously mentioned acrylic-saccharide monomers include poly(2-N-methacrylamido-2-deoxy-D-glucose), poly(3-N-methacrylamido-3-deoxy-D-glucose), poly(6-N-methacrylamido-6-deoxy-D-glucose), poly(6-O-methacrylamido-D-glucose), or poly(6-O-vinyl-D-galactose).

Polymerization of monomer-linker units, where the monomer portion of the polymer is derived from a vinyl ether monomer unit, may be carried out under acid-catalyzed conditions. Catalysts which may be used include titanium trichloride, titanium tetrachloride, aluminum trichloride, boron trifluoride etherate and the like in hexane, tetrahydrofuran, or ether solution and the like, and used in an amount of about 1 mole percent to about 20 mole percent based on the monomer, preferably about 1 mole percent to about 10 mole percent. The temperature of the polymerization under acid-catalyst conditions is about −70° to about 70° C., preferably about −20° to about 30° C.

Another way of making the polymer protein compound of the invention is to react the protein with the linker to form a derivatized protein; and thereafter react the derivatized protein with polymerizable group to form a protein-linker-monomer which is polymerized in excess of monomer containing linkers to form the polymer protein compound of the invention.

Yet another way of making the polymer protein compound of the invention, which is an important aspect of this invention, is to react the protein with the monomer containing a linker to form a protein-linker-monomer and thereafter polymerize the protein-linker-monomer in an excess of monomer containing linker to form the polymer protein compound of the invention, see below. Each of these synthetic routes are shown below.

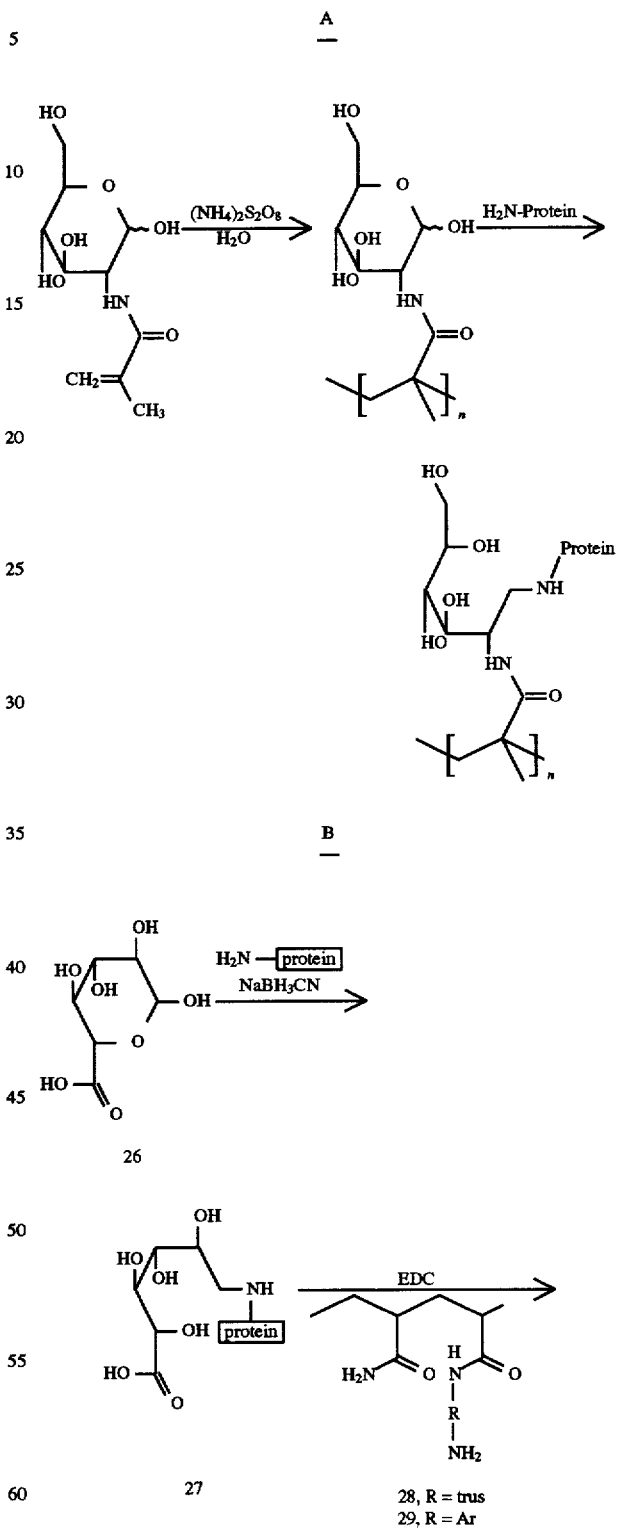

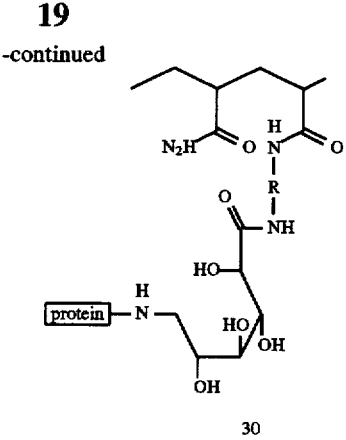

30

C

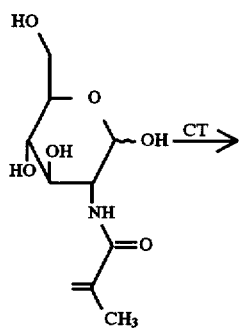

I

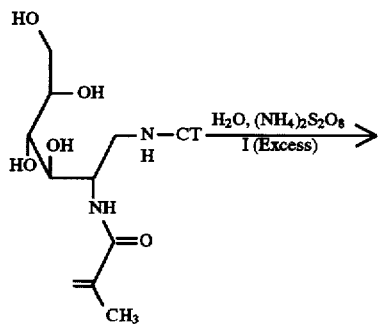

II

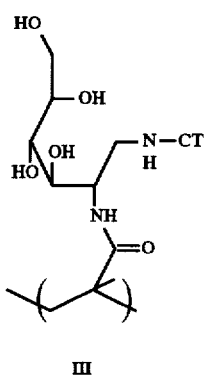

III

CT = α-Chymotrypsin.

A protein carbohydrate which includes an amine conjugate polymer can be prepared by the reaction of D-glucuronic acid (26) and a protein in the presence of sodium cyanoborohydride to give 27. Coupling of 27 to an amino-containing polymer such as Enzyacryl AH (28, R=null, null meaning covalent bond) or Enzyacryl AA (29, R=1,4-phenylene) with 1-ethyl-3-(3'N,N-dimethylaminopropyl) carbodiimide (EDC) gives the conjugate 30.

The individual linker also may be reacted or grafted onto a polymer chain with the protein thereafter being reacted or grafted onto the linker on the polymer chain. Where the polymer chain has been formed from an acrylic monomer the chain can have the following formula:

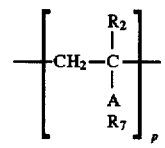

the above repeating units are derived from the monomers which provide the acrylic polymer as defined above.

Where linkers are attached to an existing polymer, the linker units can be attached or grafted onto the polymer chain with lipase at about 4° C. to about 60° C., preferably about 37° C., in borate, acetate, bicarbonate or phosphate buffer as the solvent. Preferably, the reaction is carried out in phosphate buffer. For example, glucose can be attached to poly(methacrylic acid) or poly(acrylic acid) with lipase in phosphate buffer. It should be noted that by treatment of the above polymer chain with a functionalized linker as prescribed herein, we will obtain the polymer as described earlier.

It should be noted that when making random, regular, or block copolymers, the monomers can be different from each other and the linkers can be different from each other also. By way of example, the comonomers as described in connection with Formula III can be independently selected from methacrylamide, acrylamide, methacrylic acid, acrylic acid, hydroxyethyl methacrylate, N-(2-hydroxypropyl) methacrylamide, and other monomers which include the reaction of a linker as described herein. These monomers when copolymerized may be joined with linkers including saccharide linkers such as mono-, di-, and trisaccharides as described herein.

Polymers from the polymerization of the monomer linker or the polymer with the linker bonded thereto may be water soluble and have an absolute molecular weight of over $4 \times 10^6$ daltons.

The resulting polymers which include the linker exhibit solubility in distilled water and in buffered water solutions. Preferably the polymer exhibits a solubility of greater than 1 mg/ml. The molecular weight of the polymer can vary from low molecular weight (<10,000 daltons) to high molecular weight (>5 million daltons) depending on the method used for the polymer preparation. The polymers also exhibit solubility in various organic solvents including acetonitrile, dimethylformamide, dioxane, and the like. The polymer can also form gels in water, buffered water, and organic solvent solutions. Cross-linked gels can be formed by reaction of the polymer with a suitable diamine under reductive amination conditions.

In using a saccharide linker in making the compounds of the invention, the saccharide linker is in equilibrium between the linear and cyclic forms. In the cyclic form it is protected. In the aldehyde linear form, it is not protected and could react with an amino functional group.

After a linker is coupled with a protein to form a linker group, the availability of an abundant number of hydroxyl groups on the linker group such as on a saccharide linker group provides enhancement of hydrophilic amino acid residue contacts.

The coupling reaction with an aldehyde group on the saccharide linker group is accomplished by treatment of a protein such as an enzyme or antibody or the like with the polymer which includes the linker, whether the polymer is a homopolymer, random or block copolymer in a buffer solution. Typically, the buffer solution is sodium borate solution, but the buffer solution can also be HEPES or phosphate buffer. Even though sodium cyanoborohydride is preferred, sodium borohydride, lithium cyanoborohydride or potassium cyanoborohydride can be used, this mild reaction is preferably carried out at a pH of about 6 to about 10, preferably about 8 to about 9.5. The reaction temperature is between about 4° C. to about 50° C., at about 2 hours to about 48 hours. Preferably, the reaction temperature is between about 20° C. and about 37° C., for about 24 hours to about 48 hours.

The coupling reaction with a lactone group on the saccharide linker group is accomplished by treatment of a protein such as an enzyme or antibody or the like with the polymer which includes the linker, whether the polymer is a homopolymer, random or block copolymer in a buffer solution. Typically, the buffer solution is sodium borate solution, but the buffer solution can also be HEPES or phosphate buffer. This mild reaction is preferably carried out at a pH of about 6 to about 10, preferably about 7 to about 9. The reaction temperature is between about 4° C. to about 50° C., at about 2 hours to about 48 hours. Preferably, the reaction temperature is between about 20° C. and about 37° C., for about 24 hours to about 48 hours.

The weight equivalents of the ingredients used in the reductive reaction coupling the protein to linker, based on the weight of the protein, is about 1 to about 100 weight equivalents of polymer and about 0.1 to about 10 weight equivalents of sodium cyanoborohydride. Preferably the amount of the ingredients used, based on the weight of the protein, is about 50 weight equivalents of polymer and about 2 weight equivalents of sodium cyanoborohydride. The progress of the reaction can be monitored by gel filtration chromatography and the yield of the reaction can be determined, for example, by measurement of the relative activity of the native enzyme and the protein polymer conjugate. Generally the yield of the coupling reaction is greater than about 25%. As will be discussed more fully below, the solubility of the compounds of the invention and their compatibility with a particular solvent system is at least in part a function of the alkyl groups on the linker group. While these alkyls may have up to 30 or more carbon atoms, organic solvents will be compatible with polymer protein compounds which include an acrylic polymer and a saccharide linker where the linker has alkyls ($R_1$ to $R_9$) having 3 to 16 carbons and the acrylic polymer is substituted with alkyls having 0 to 4 carbons. Where the alkyls R1 to $R_9$ have two carbons and the substitution on the acrylic polymer does not exceed a two carbon alkyl, the polymer protein compounds of the invention may be water soluble.

An alternative way of preparing the compounds of this is to attach the polymerizable saccharides, especially monosaccharides to the protein first. The smaller size of the functional groups substantially reduces the amount of steric hinderance which may occur about densely packed lysine residues in a protein. Additionally lysine residues located inside a cleft, which are not accessible by bulky polymer-saccharide chains, become accessible and may be coupled by small monomeric units. As a result, a greater number of lysine residues in a protein are bonded to saccharides. Once coupled, the monomeric units can be polymerized (as described in C above) to produce a carbohydrate polymer bonded to an enzyme with a higher degree of substitution between polymer and protein. This polymerization step also provides a great deal of control in the nature of the coupled product. By introducing a varied amount of uncoupled monomer to the polymerization step, the length of the polymer chain between lysine residues of the protein can be controlled. Furthermore, the concentration of the enzyme can be altered in the polymerization step to effect the amount of intermolecular coupling.

In this connection, enzymes were coupled to 2-N-methacrylamido-D-glucose monomer and were polymerized by free radical polymerization conducted in an aqueous solution using ammonium persulfate as the initiator. After 12 hours at room temperature, the copolymerized enzymes are separated by HPLC chromatography. High molecular weight fractions of the enzyme bonded to the saccharide linker polymer were collected and desiccated by lyophilization, at which point the polymer protein product could be stored indefinitely.

The following reactions are exemplary of making the polymer protein compounds of the invention with different A, B and L groups as defined above.

Where

A=—CH$_2$O—

B=—NH—

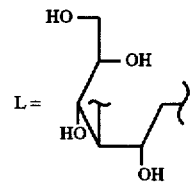

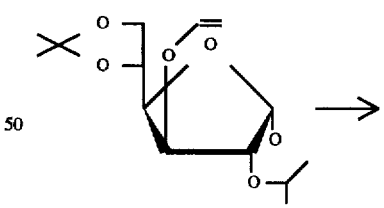

1

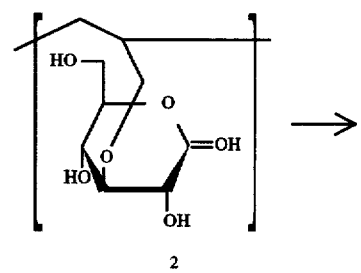

2

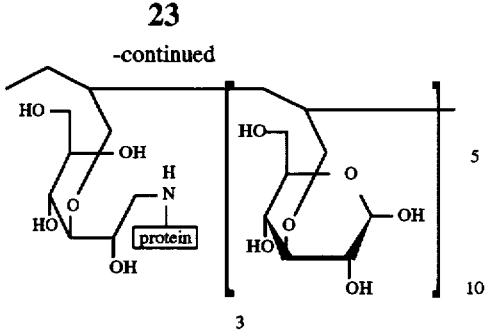

Compound 1 can be prepared by acid catalyzed methods to give 2 using, by way of example, by using boron trifluoride etherate or titanium chloride as catalysts in solvents such a diethyl ether or tetrahydrofuran. Compound 3 is prepared by standard reductive amination.

Where

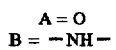

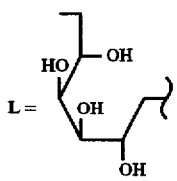

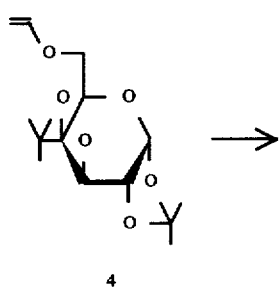

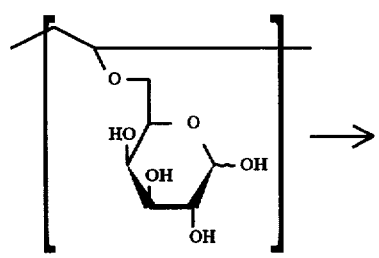

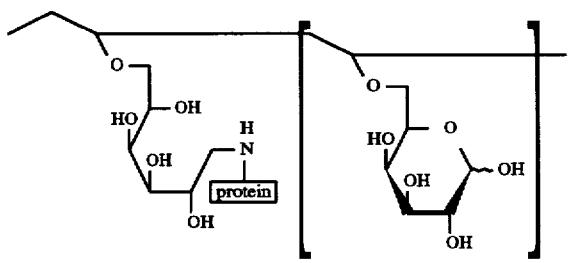

Compound 5 may be made by acid catalyzed polymerization of 4. Compound 5 when treated with the desired protein and sodium cyanoborohydride in aqueous solution gives 6.

Where

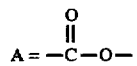

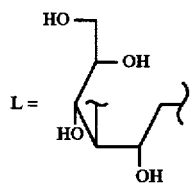

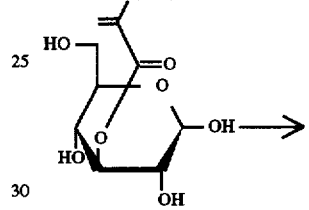

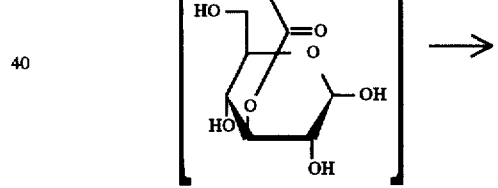

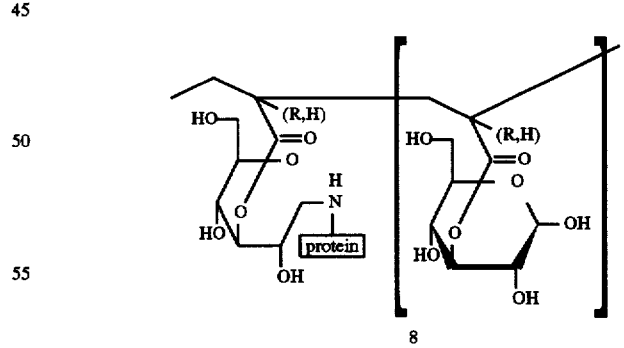

A protein conjugate with an ester linkage between the polymer backbone and the linker can be prepared by free-radical polymerization of the monomer 7 to give 8 which, when treated with the desired protein and sodium cyanoborohydride in aqueous solution gives the conjugate 9.

Where

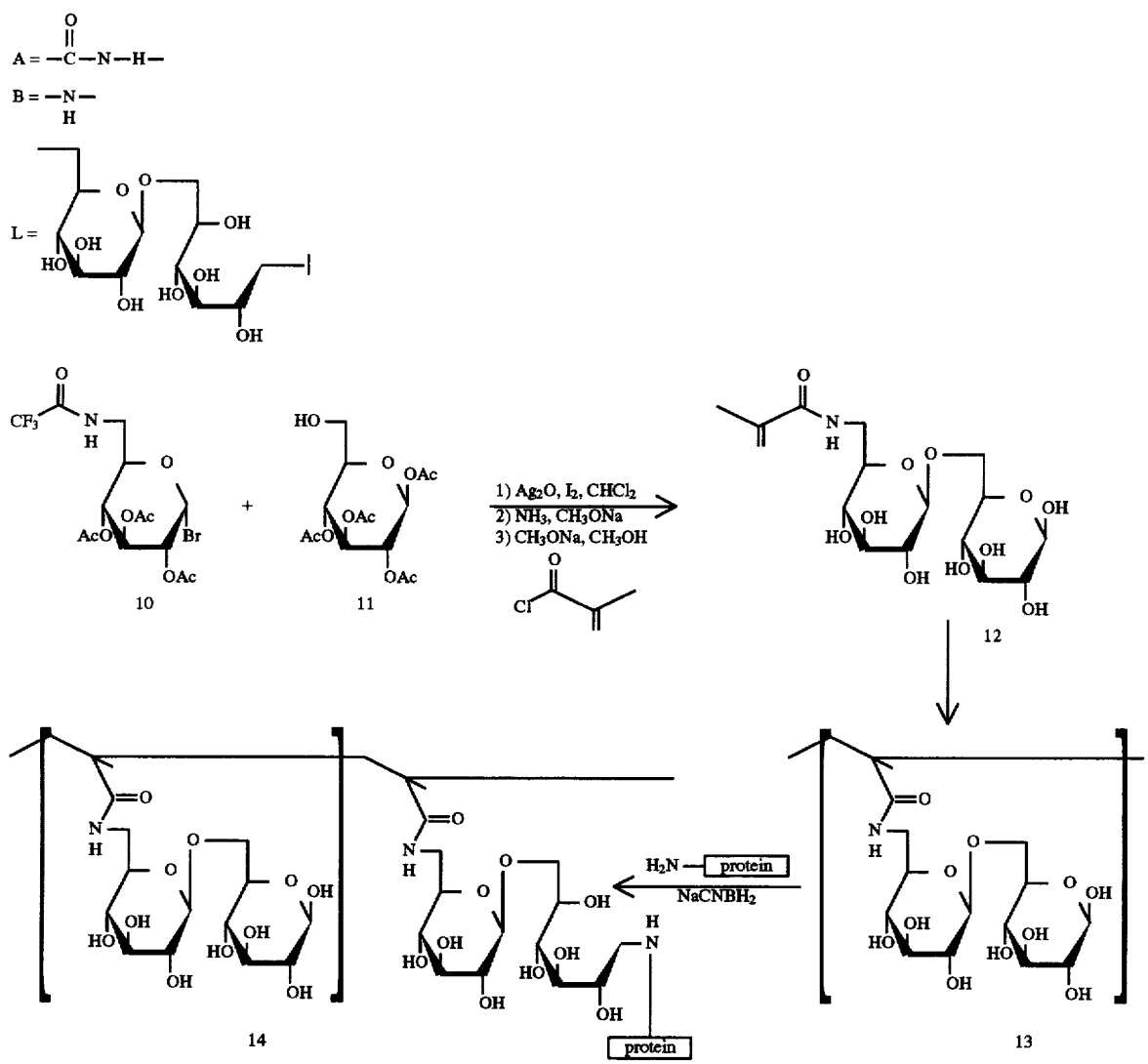

A protein conjugate with an amide linkage between the polymer backbone and a saccharide linker which contains a ring in addition to the open form of the sugar (via a disaccharide) can be prepared by attachment of a polymerizable side-group to an amino-substituted disaccharide followed by its polymerization and reductive amination with a protein. For example, a polymerizable amino-substituted disaccharide (12) can be prepared by the silver oxide mediated coupling of 10 with 11 followed by removal of the acetate groups with ammonia and catalytic sodium methoxide. Subsequent treatment with methacryloyl chloride in methanol in the presence of sodium methoxide gives 12. Polymerization of 12 using ammonium persulfate in water gives the polymer 13 which can be coupled to various proteins using reductive amination methodology to give the conjugate 14.

Where

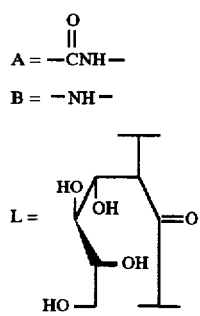

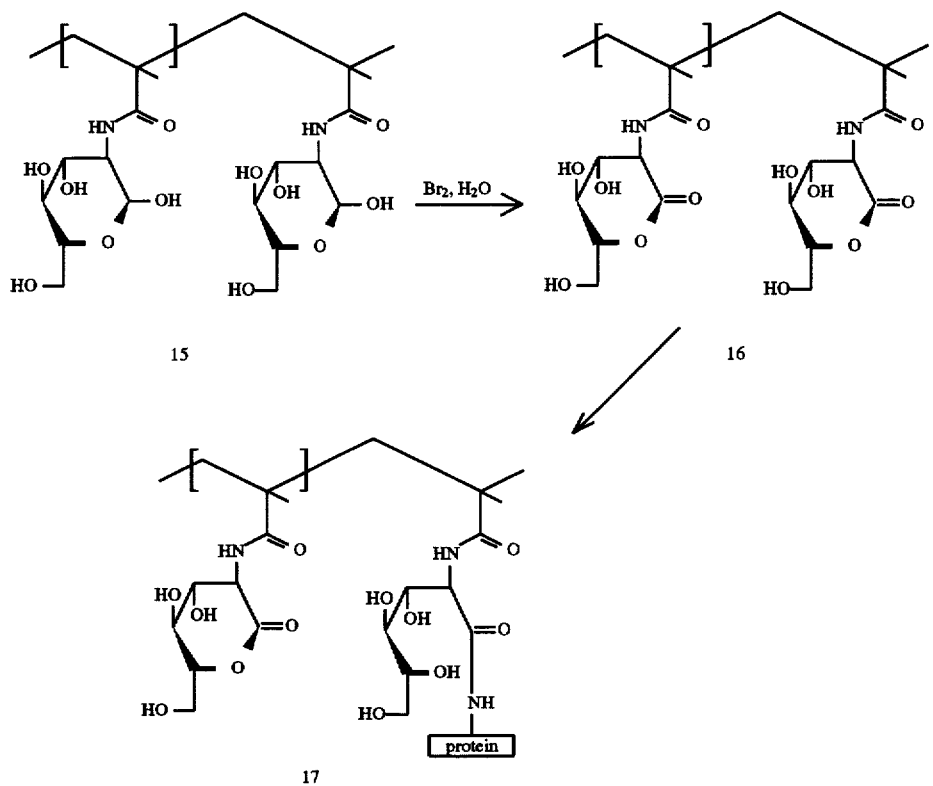

Preparation of a lactone containing polymer and its use for preparation of a conjugate can be accomplished by treatment of poly(2-methacrylamido-2-deoxy-D-glucose) with bromine in water to give poly(2-methacrylamido-2-deoxy-D-gluconolactone) which can be used directly to couple with a desired protein in buffered solution, for example, borate or phosphate buffers, to give the conjugate 17.

Solubility Control

Controlling the solubility of the polymer protein compounds of the invention is another important aspect of this invention. Generally this solubility may be controlled, for example, by cross-linking, by formation of hydrogels or by attaching the polymers to a glass as shown below.

Gels of the polymer can be made by using high concentrations of monomer with the least amount of solvent effective for solubilizing the monomer or monomer linker for polymerizing the monomer or monomer linker at a given pH. Using low amounts of water as a solvent for polymerization is particularly effective for producing hydrogels of the compounds of the invention.

For example, control of the reaction conditions for the polymerization of saccharides substituted with polymerizable side-groups can effect the formation of such a hydrogel rather than a water-soluble polymer. Typically, a polymerization solution containing a 0.5 to 1.5M concentration of the monomer, preferably 0.8M concentration, with 0.005 to 0.1M concentration of free-radical initiator, preferably 0.01M concentration, at 1° C. to 25° C., preferably 5° C., over a period of 1 h to 48 h, preferably 18 h, gives a gel containing 70 to 95% water, preferably 85% water.

Cross-linking the compounds of the invention is another way to control their solubility and to make them insoluble. In this context, the compounds of the invention can be further functionalized, such as at the linker group, to make them reactive with a cross-linker. In one aspect, the polymer and linker may be cross-linked to form an insoluble gel before protein is bonded to other unreacted linkers on the polymer or after the protein is bonded to the linker on the polymer. Further, because a protein can be bonded to more than one polymer through a linker group, a cross-linked polymer or a polymeric matrix may be formed through bonding a protein to multiple polymers or through cross-linking the compounds as shown below.

The soluble form of the compounds can be made for ease of preparation and then be made insoluble. By way of example, it is highly desirable to use water soluble poly(2-N-methacrylamido-2-deoxy-D-glucose) with an average molecular weight of greater than 300,000 daltons for preparation of the conjugate, while it is most desirable to use water soluble poly(2-N-methacrylamido-2-deoxy-D-glucose) with an average molecular weight of greater than $1 \times 10^6$.

Thereafter, as shown below, an insoluble form of the conjugate is the reaction of the polymer conjugate (15) with a diamine linker, such as 1,6-hexanediamine, with sodium cyanoborohydride to give the cross-linked material shown as 32. The level of cross-linking, preferably about 1 percent, affects the rigidity of the gel formed.

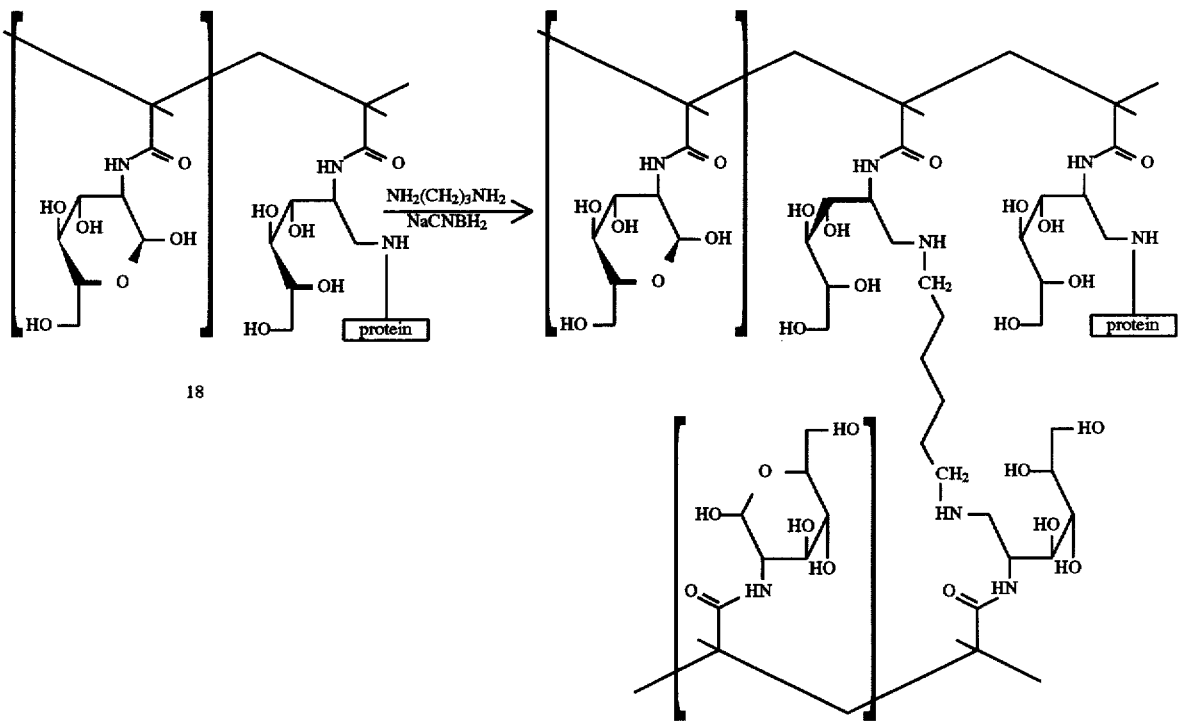

32
CROSS-LINKING TO FORM A GEL

An alternative method for formation of an insoluble form of the conjugate is the reaction of the polymer protein conjugate (15) with alkylamine glass using EDC to affix the conjugate to the solid support giving 31.

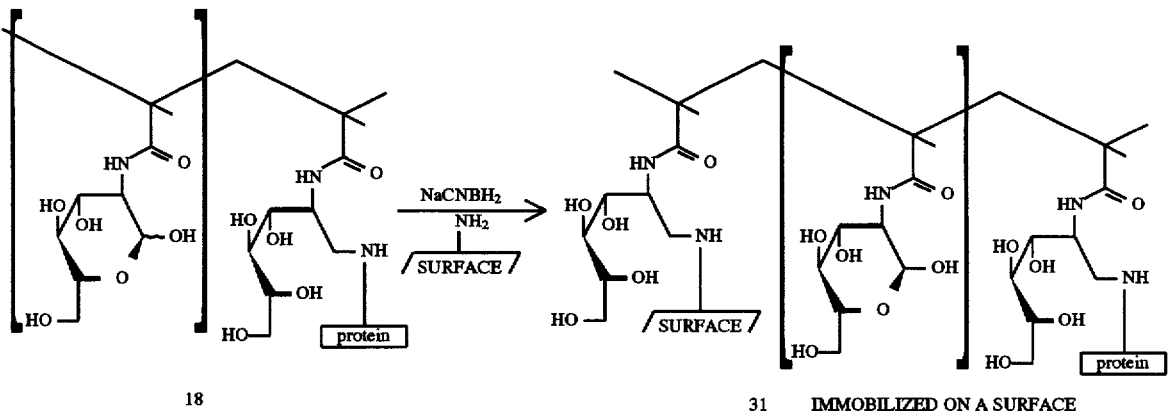

31   IMMOBILIZED ON A SURFACE

Stabilizing Proteins, Making Peptide Bonds And Use Of The Stabilized Proteins In Assays Hostile environments affect the activity of proteins including enzymes. According to the method of the invention, an intended functional property is either maintained to be at least equal to the native protein or it is enhanced over a reduced activity that the protein would have in a hostile environment. The method of the invention particularly can be seen in connection with maintaining or enhancing the half life of an enzyme or antibody.

As used herein, "half life" means the time it takes for an enzyme to lose one half of a given activity. In the method of the invention where the enzyme is incorporated into a compound of the invention, the half life of the enzyme in a hostile environment will be at least greater and preferably at least about 110% or more of the half life of the native enzyme in the same harsh environment. Indeed, most preferably the half life of the enzyme when a part of the polymer protein compound of the invention will be enhanced from about 110% to about 1000% or more over that of the native enzyme in a hostile environment which would reduce the half life of the native enzyme.

The stability of antibodies also is improved. In this aspect of the invention, the "half life of an antibody" means the time it takes for an antibody to lose one half of its ligand binding ability. According to the invention, when the antibody is incorporated into the compound of the invention, the half life of the antibody in a hostile environment will be at least about 110% or more of the half life of the antibody in the same hostile environment. As with the enzyme, most preferably the half life of the antibody when made into a polymer protein compound of the invention will be enhanced from about 110% to about 1000% or more over that of the native antibody in a hostile environment which would reduce the activity of the native antibody.

Figure 2:
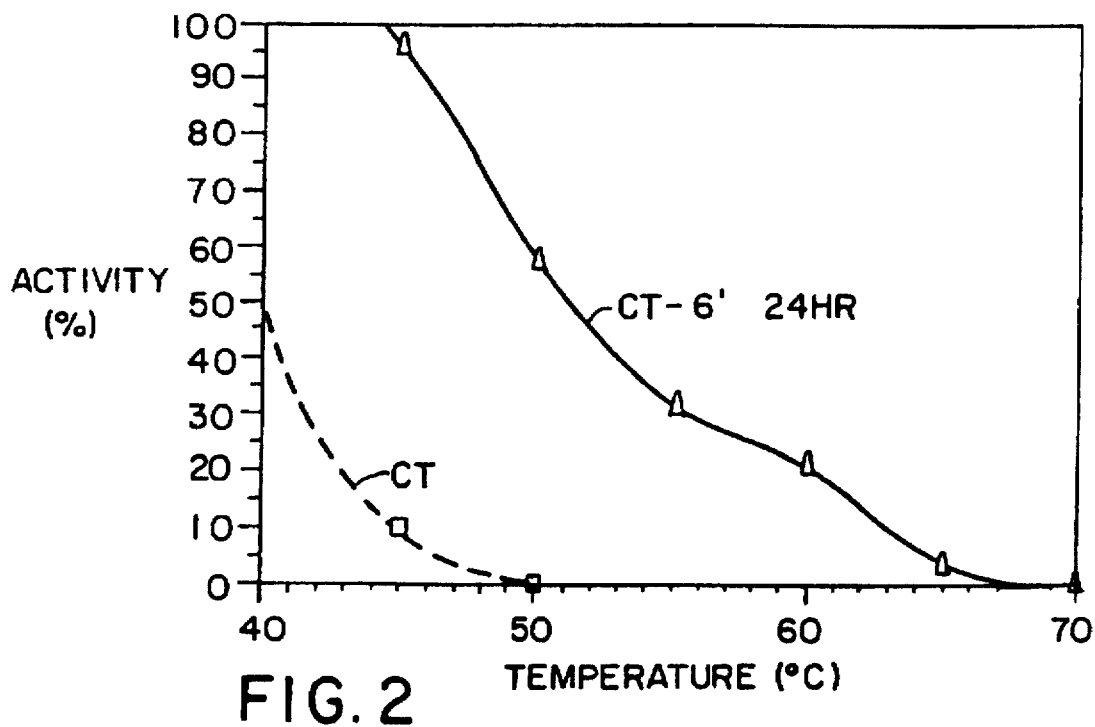
FIG. 2 describes the stability of the trypsin-polymer conjugate and native trypsin in buffer and water.

Exposure to elevated temperatures and proteolytic attack can affect the activity of enzymes. Native α-chymotrypsin is deactivated immediately when exposed to about 60° C. borate buffer solution. The α-chymotrypsin-poly(6-N-methacrylamido-6-deoxy-D-glucose) conjugate made herein maintains greater than 30 percent activity after exposure to about 60° C. borate buffer solution for about 1 hour, greater than 20 percent activity after about 6 hours, and greater than 15 percent activity after about 15 hours, see FIG. 2.

Native trypsin enzyme loses greater than 90 percent of its activity within 1 hour when exposed to a temperature of 55° C. The polymer-trypsin conjugates of poly(2-N-methacrylamido-2-deoxy-D-glucose) and poly(6-N-methacrylamido-6-deoxy-D-glucose), for example after exposure to a temperature of 55° C. for one hour retained approximately 25 and 35 percent of its activity, respectively see FIG. 3.

The lack of buffer is another factor which can result in denaturation or inactivation of enzymes. The trypsin enzyme in a phosphate buffer solution does not lose its activity quickly. The enzyme loses approximately 25 percent of its activity after 7 days. However, when the native trypsin is placed in a distilled water solution the enzyme has less than 20 percent of its activity after 7 days. In contrast, the trypsin-poly(2-N-methacrylamido-2-deoxy-D-glucose) conjugate does not lose activity over a seven day period in a buffered or distilled water solution, see FIG. 4.

The activity of α-chymotrypsin in buffer solution at about 45° C. falls to about 75% of its initial activity within about 10 minutes, and less than about 10 percent after about 9 hours, and to about 0 percent after about 18 hours. The activity of α-chymotrypsin in distilled water solution falls to approximately 30% activity within about 10 min and falls to about 0 percent after about 9 hours. However when α-chymotrypsin is stabilized by the materials described in this invention, the activity at about 45° C. is maintained at greater than 80% over about 18 hours in both buffer and distilled water solutions, see FIG. 1.

Enzymes which can be part of the polymer protein compounds of the invention include enzymes related to the production of fructose, such as glucose isomerase, which operates at 60° to 65° C., hydrolysis of starch by α-amylase, which occurs at 85° to 110° C. and resolution of D,L-amino acids by amino acetolase at 50° C. Other enzymes which can be a part of the polymer protein compounds of the invention are nucleases, including endonucleases.

Enzymes which can be stabilized as described here include oxidoreductases, transferases, dehydrogenases, transaminases, peptidases, hydrolases, isomerases, mutases and the like. In addition to enzymes already described, other enzymes which could be stabilized herein include but are not limited to malate dehydrogenase; creatine kinase (CK, CPK); alkaline phosphatase (AP, ALP, ALK-phos); aspartate aminotransferase (AST, OT, GOT); alanine aminotransferase (ALT, PT, SGPT); gamma glutamyl transpeptidase (gammaGT, gammaGTP); glutamic oxalaoetic transaminase (SGOT); glutamic pyruvic transaminase (GTP); alpha amylase; beta amylase; lactate dehydrogenase (LD, LDH, lactic dehydrogenase); glucose-6-phosphate dehydrogenase (G6PDH); hexokinase (HK); glucose dehydrogenase; glucose oxidase; peroxidase (HRP, HPO, HRPO, PO); glycerol dehydrogenase; glutamate dehydrogenase, cholesterol oxidase; cholesterol esterase; lipase; uricase; urease; glycerol kinase; aldolases; synthetases; nucleases; polymerases; and the like.

Additionally, the compounds of the invention could be used in applications of enzymatic analysis represented by the diagnostic reagents used to determine and quantitate the following constituents in fluids include but are not limited to glutamic-oxalacetic transaminase (SGOT); glutamic-pyruvic transaminase (SGPR); lactic dehydrogenase (LDH); creatine phosphokinase (CPK); alpha-hydroxybuteric dehydrogenase (alpha-HBD); glucose (via hexokinase-glucose-6-phosphate dehydrogenase, glucose oxidase, glucose dehydrogenase); and blood urea nitrogen (BUN).

Antibodies or antigens may be coupled to the polymer with linkers by treating, based on the weight of the antibody or antigen, about 1 to about 100 weight equivalents of polymer and about 0.1 to about 10 weight equivalents of sodium cyanoborohydride in 0.05M sodium borate buffer. The reaction temperature is between about 25° C. to about 50° C., for about 2 to about 48 hours. Preferably the coupling reaction is carried out, based on the weight of the antibody or antigen, with about 50 weight equivalents of polymer and about 2 weight equivalents of sodium cyanoborohydride in 0.05M sodium borate buffer at about 37° C. for about 48 hours. The antibody-polymer and antigen-polymer complex can be isolated using gel filtration chromatography. The concentration of antibody-polymer and antigen-polymer complex is determined by measurement of optical density.

When incorporated into compounds of the invention, antibodies and antigens maintained their competency when incorporated into normal enzyme-linked immunosorbent assay methodology (Tables 3 and 4 in Example 11). Furthermore, conjugated antibody and antigen performed similarly to nonconjugated antibody and antigen in competition assays (Table 5).

Additionally, the use of antibodies and antigens incorporated into the compounds of the invention allows the detection of antigens in non-optimal aqueous solutions and organic solvents. Potentially, incorporation of antibody and reporter enzyme in the same conjugate would result in an improvement of the ELISA assay by eliminating the need to add a second antibody conjugated to an enzyme.

The polymer herein can also be used to synthesize peptide bonds. Typically, equimolar solutions containing modified amino acid(s) are dissolved in a solvent system containing an organic solvent such as dioxane or THF (tetrahydrofuran), or a tertiary amine such as $(iPr)_2NEt$, to form an amino acid mixture. More preferably, the organic solvent is acetonitrile. The solutions dissolved in the solvent system are defined herein as amino acid acceptor and amino acid donor solutions. Examples of such solutions can be found in Table 2 of Example 10.

A conjugated enzyme such as protease (the enzyme incorporated into one of the compounds of the invention) may be added to the amino acid mixture in an amount of about $10^{-6}$ to about $10^{-1}$ mole fraction relative to the amount of amino acid. The conjugated enzyme can be prepared as in Example 8. The reaction is performed at from about 0° to 70° C., at about 1 to about 24 hours. The enzyme polymer conjugate is removed from the formed peptide by filtering and the solvent is evaporated to obtain the resulting peptide.

The Examples herein are for illustrative purposes only and are not meant to narrow the scope of the invention herein.

EXAMPLE 1

Preparation of 3-amino-3-deoxy-D-glucose hydrochloride

A water-soluble monosaccharide suitable for this application was prepared by treatment of 3-amino-3-deoxy-1,2:5, 6-diisopropylidine-D-glucose (1.78 mmol, 0.46 g) in 150 mL 1N HCl (prepared with triply glass distilled water) with stirring under argon at room temperature for 4 days. The resulting pale yellow solution was filtered and evaporated to a light brown brittle froth. The froth was dissolved in water, stirred with activated charcoal, and filtered through Celite 545 yielding a colorless filtrate. Removal of the water in vacuo gave 0.41 g (100%) of a pale yellow glassy solid of 3-amino-3-deoxy-D-glucose hydrochloride.

EXAMPLE 2

Preparation of 3-deoxy-3-N-methacrylamido-D-glucose

A water-soluble monomer suitable for this application was prepared by treatment of 3-amino-3-deoxy-D-glucose hydrochloride with sodium methoxide (prepared by the addition of sodium (3.35 mmol, 0.077 g) to 7 mL methanol) added dropwise to a solution of 3-amino-3-deoxy-D-glucose hydrochloride (1.84 mmol, 0.397 g) in 6 mL of methanol. The mixture was stirred at room temperature for 30 min. To this solution was then added methacryloyl chloride (3.17 mmol, 0.31 mL) dropwise alternately with a further equivalent of sodium methoxide solution [3.87 mmol (0.089 g) sodium in 7 mL methanol]. The mixture was stirred for 1 hour resulting in a pH=11. The mixture was filtered and the filtrate pass through 12 g Amberlite IR120H$^+$ acid ion exchange resin (prewashed with 1N hydrochloric acid, water, and methanol) onto sodium bicarbonate. The eluant was filtered and the solvent removed in vacuo resulting in 0.65 g (97%) of a yellow solid.

EXAMPLE 3

Preparation of 6-amino-6-deoxy-D-glucose hydrochloride

A water-soluble monosaccharide suitable for this application was prepared by treatment of 6-amino-6-deoxy-1,2-isopropylidine-D-glucose (1.98 mmol, 0.51 g) in 150 mL 1N HCl (prepared with triply glass distilled water) with stirring under argon at room temperature for 2 days. The resulting pale yellow solution was filtered and evaporated to a light brown brittle froth. The froth was dissolved in water, stirred with activated charcoal, and filtered through Celite 545 yielding a colorless filtrate. Removal of the water in vacuo gave 0.49 g (100%) of a pale yellow glassy solid of 6-amino-6-deoxy-D-glucose hydrochloride.

EXAMPLE 4

Preparation of 6-deoxy-6-N-methacrylamido-D-glucose

A water-soluble monomer suitable for this application was prepared by treatment of 6-amino-6-deoxy-D-glucose hydrochloride (0.49 g, 2.29 mmol) with sodium methoxide (prepared by the addition of sodium (3.70 mmol, 0.085 g) to 7 mL methanol) added dropwise to a solution of 6-amino-6-deoxy-D-glucosamine hydrochloride (1.84 mmol, 0.397 g) in 16 mL of methanol at 0° C. The mixture was stirred at room temperature for 30 min. To this solution was then added methacryloyl chloride (4.61 mmol, 0.45 mL) dropwise alternately with a further equivalent of sodium methoxide solution [5.70 mmol (0.131 g) sodium in 7 mL methanol]. The mixture was stirred for 1 hour resulting in a pH=9. The mixture was filtered and the filtrate passed through 12 g Amberlite IR120H$^+$ plus acid ion exchange resin (prewashed with 1N hydrochloric acid, water, and methanol) onto sodium bicarbonate. The eluant was filtered and the solvent removed in vacuo resulting in 0.54 g (95%) of a yellow solid.

EXAMPLE 5

Preparation of poly(2-N-methacrylamido-2-deoxy-D-glucose)

A water-soluble individual backbone-linker unit was prepared by the addition of 47.97 g (0.22 mole) of glucosamine hydrochloride to 12.16 g (0.23 mole) of sodium methoxide in 500 mL of methanol. A second solution of 17.1 g (0.32 mole) of sodium methoxide in 600 mL of methanol was added concurrently with 24 mL (0.25 mole) of methacryloyl chloride. The cloudy mixture was filtered and the filtrate evaporated to dryness yielding 77 g containing 2-N-methacrylamido-2-deoxy-D-glucose and sodium chloride. This material can be used directly for preparation of polymeric material. Removal of sodium chloride is accomplished by passage of the filtrate through Amberlite IR120H$^+$ onto sodium bicarbonate followed by filtration and removal of the solvent in vacuo gave a quantitative yield of the individual backbone-linker unit.

Free-radical polymerization of 2-N-methacrylamido-2-deoxy-D-glucose was carried out under an inert atmosphere in quadruply distilled and freeze-thaw-degassed water solution. A solution of 5.00 g (0.0202 mole) of 2-N-methacrylamido-2-deoxy-D-glucose was dissolved in 10 mL of water. To this solution 503 mg (2.21 mmol) of ammonium persulfate dissolved in 1 mL of water was quickly added and the solution allowed to stir at 20° C. for 17 hours. The polymer was precipitated by pouring the reaction solution into 1000 mL of methanol. The solution was allowed to settle, the solution was decanted and the polymer collected by filtration. The solid was washed with methanol and dried in vacuo to give 5.0 g (100%) of a water-soluble polymer with a molecular weight of $4.36 \times 10^6$ with a polydispersity of 1.3.

EXAMPLE 6

Preparation of poly(3-N-methacrylamido-3-deoxy-D-glucose)

The procedure of EXAMPLE 5 was repeated in every essential detail except that 1.92 g (7.76 mmol) 3-N-methacrylamido-3-deoxy-D-glucose was polymerized in 40 mL of water with 182.2 mg (0.80 mmol) of ammonium persulfate at 30° C. giving 1.61 g (84%) of a water-soluble polymer with a molecular weight of $4.42 \times 10^6$ with polydispersity of 1.4.

EXAMPLE 7

Preparation of poly(6-N-methacrylamido-6-deoxy-D-glucose)

The procedure of EXAMPLE 5 was repeated in every essential detail except that 1.76 g (7.21 mmol) 6-N- methacrylamido-6-deoxy-D-glucose was polymerized in 50 mL of water with 170 mg (0.75 mmol) of ammonium persulfate at 20° C. giving 800 mg (45%) of a water-soluble polymer with a molecular weight of $5.74 \times 10^6$ with a polydispersity of 1.2.

EXAMPLE 8

Preparation of Enzyme-Polymer Conjugates (a) Trypsin-Polymer Conjugates (i) Trypsin-poly(2-N-methacrylamido-2-deoxy-D-glucose) conjugate A protein polymer conjugate of poly(2-N-methacrylamido-2-deoxy-D-glucose) and trypsin was prepared by the reductive amination procedure as shown below:

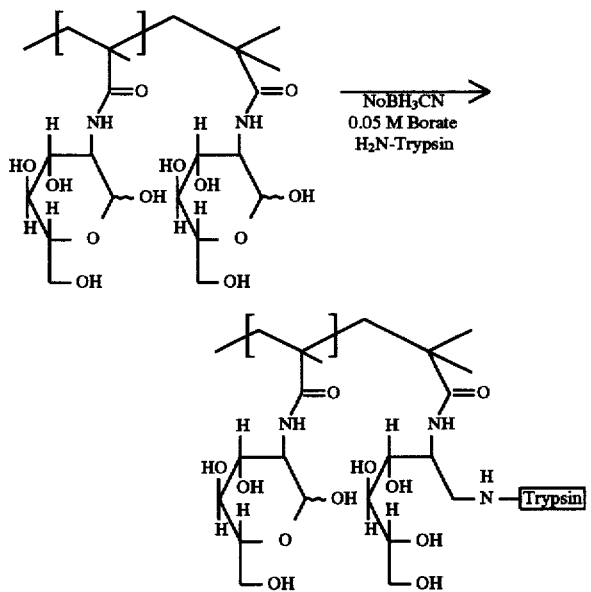

To 20 mL of a 0.05M sodium borate solution at pH 8 was added 148 mg ($3 \times 10^{-8}$ mole) of poly(2-N-methacrylamido-2-deoxy-D-glucose) with 30 mg ($1.2 \times 10^{-6}$ mole) of trypsin and 10 mg ($9.55 \times 10^{-4}$ mole) of purified sodium cyanoborohydride. The solution was placed in a shaking water bath at 60 oscillations/min at 35° C. for 48 hours. The progress of the reaction was followed by gel filtration chromatography using 0.05M sodium borate as the eluent on Sephacryl S-200 with a flow rate of 1.5 mL/min. Dialysis of the solution using Spectra Por CE 100K MWCO membrane against $2 \times 250$ mL of 0.05M sodium borate at pH 8 for 14 hours gave a 42% yield of active stabilized trypsin-polymer conjugate.

The yield of the active enzyme was determined by comparison of the relative activity of the native trypsin and the trypsin-polymer conjugate for N-succinyl-Ala-Ala-Pro-Phe p-nitroanilide as the substrate in 0.05M sodium phosphate buffer at pH 8 containing 10% methanol. Kinetic analyses of the trypsin-polymer conjugate and native trypsin for $k_{cat}$ and $K_m$ are listed in Table 1.

(ii) Trypsin-N-poly(3-N-methacrylamido-3-deoxy-D-glucose) conjugated

The procedure of EXAMPLE 8(a) (i) was repeated in every essential detail except that poly(3-N-methacrylamido-3-deoxy-D-glucose) was used instead of poly(2-N-methacrylamido-2-deoxy-D-glucose).

(iii) Trypsin-poly(6-N-methacrylamido-6-deoxy-D-glucose) conjugate

The procedure of EXAMPLE 8(a) (i) was repeated in every essential detail except that poly(6-N-methacrylamido-6-deoxy-D-glucose) was used instead of poly(2-N-methacryl-amido-2-deoxy-D-glucose).

(b) α-Chymotrypsin-Polymer Conjugates (i) α-Chymotrypsin-poly(2-N-methacrylamido-2-deoxy-D-glucose) conjugate The procedure of EXAMPLE 8(a) (i) was repeated in every essential detail except that α-chymotrypsin was used instead of trypsin.

(ii) α-Chymotrypsin-poly(3-N-methacrylamido-3-deoxy-D-glucose) conjugate

The procedure of EXAMPLE 8(a) (i) was repeated in every essential detail except that poly(3-N-methacrylamido-3-deoxy-D-glucose) was used instead of poly(2-N-methacrylamido-2-deoxy-D-glucose) and α-chymotrypsin was used instead of trypsin.

(iii) α-Chymotrypsin-poly(6-N-methacrylamido-6-deoxy-D-glucose) conjugate

The procedure of EXAMPLE 8(a) (i) was repeated in every essential detail except that poly(6-N-methacrylamido-6-deoxy-D-glucose) was used instead of poly(2-N-methacrylamido-2-deoxy-D-glucose) and a-chymotrypsin was used instead of trypsin.

(c) BPN'-Subtilisin-Polymer Conjugates (i) BPN'-Subtilisin-poly(2-N-methacrylamido-2-deoxy-D-glucose conjugate The procedure of EXAMPLE 8(a) (i) was repeated in every essential detail except that BPN'-subtilisin was used instead of trypsin.

(ii) BPN'-Subtilisin-poly(3-N-methacrylamido-3-deoxy-D-glucose) conjugate

The procedure of EXAMPLE 8(a) (i) was repeated in every essential detail except that poly(3-N-methacrylamido-3-deoxy-D-glucose) was used instead of poly(2-N-methacrylamido-2-deoxy-D-glucose) and BPN'-subtilisin was used instead of trypsin.

(iii) BPN'-Subtilisin-poly(6-N-methacrylamido-6-deoxy-D-glucose) conjugate

The procedure of EXAMPLE 8(a) (i) was repeated in every essential detail except that poly(6-N-methacrylamido-6-deoxy-D-glucose) was used instead of poly(2-N-methacrylamido-2-deoxy-D-glucose) and BPN'-subtilisin was used instead of trypsin.

(d) Carlsberg-Subtilisin-Polymer Conjugates (i) Carlsberg-Subtilisin-poly(2-N-methacrylamido-2-deoxy-D-glucose) conjugate The procedure of EXAMPLE 8(a) (i) was repeated in every essential detail except that Carlsberg-subtilisin was used instead of trypsin.

(ii) Carlsberg-Subtilisin-poly)3-N-methacrylamido-3-deoxy-D-glucose) conjugate

The procedure of EXAMPLE 8(a) (i) was repeated in every essential detail except that poly(3-N-methacrylamido-3-deoxy-D-glucose) was used instead of poly(2-N-methacrylamido-2-deoxy-D-glucose) and Carlsberg-subtilisin was used instead of trypsin.

(iii) Carlsberg-Subtilisin-poly(6-N-methacrylamido-6-deoxy-D-glucose) conjugate

The procedure of EXAMPLE 8(a) (i) was repeated in every essential detail except that poly(6-N-methacrylamido-6-deoxy-D-glucose) was used instead of poly(2-N-methacrylamido-2-deoxy-D-glucose) and Carlsberg-subtilisin was used instead of trypsin.

TABLE 1

$K_m$ and $k_{cat}$ of Enzyme-Polymer Conjugates

| Enzyme | $K_m$(mM) | $k_{cat}$(seconds$^{-1}$) |
|---|---|---|
| α-chymotrypsin | 0.040 | 33 |
| CPC-α-chymotrypsin | 0.046 | 20 |
| trypsin | 0.760 | 0.9 |
| CPC-trypsin | 0.890 | 1.2 |
| BPN'-subtilisin | 0.240 | 83 |
| CPC—BPN'-subtilisin | 0.350 | 76 |
| Carlsberg-subtilisin | 0.251 | 420 |
| CPC-Carlsberg-subtilisin | 0.580 | 370 |

*CPC is the carbohydrate protein conjugate for poly-(2-N-methacrylamido-2-deoxy-D-glucose)-enzyme conjugate.

EXAMPLE 9

Figure 3:
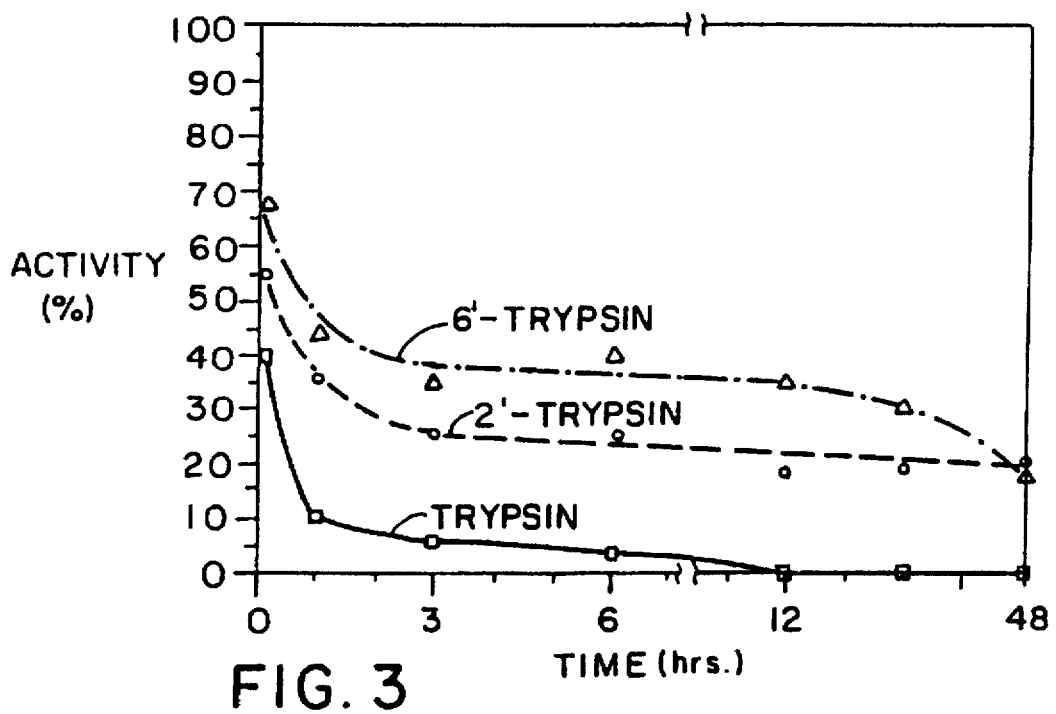
FIG. 3 describes the activity over time of trypsin, poly (2-N-methacrylamido-2-deoxy-D-glucose)-trypsin conjugate and poly(6-N-methacrylamido-6-deoxy-D-glucose)-trypsin conjugate at 55° C.

Temperature Stability of the Enzyme-Polymer Conjugates (a) Temperature Stability of α-Chymotrypsin-Polymer Conjugates (i) Stability of the Poly(2-N-methacrylamido-2-deoxy-D-glucose-)-α-Chymotrypsin Conjugate Activity studies at elevated temperatures were carried out in 5 mL round-bottomed flasks containing 3 mL of 0.05M sodium borate solution of α-chymotrypsin-polymer conjugate or α-chymotrypsin at an approximate concentration of protein of 0.01 mg/mL. The solutions were assayed at 25° C. for their activity and the flasks were then immersed in oil baths at 45°, 50°, 55°, 60°, 65°, 70° C. Aliquots (0.02 to 0.3 mL) were removed from each flask and the activity determined (as described in Example 8(a) (i)) at 25° C. after 10 min, 1 hour, 3 hours, 6 hours, 12 hours, 24 hours, and 48 hours. The activity of the α-chymotrypsin-polymer conjugate and α-chymotrypsin after exposure to elevated temperatures for 6 hours are shown in FIG. 3. Examination of FIG. 3 clearly shows that the activity of the α-chymotrypsin-polymer conjugate is maintained at greater than 50% of its initial activity after 6 hours at 50° C. while the activity of native α-chymotrypsin is completely lost. In addition, the use of the enzyme has been extended to greater than 60° C. over a 6 hour period.

Figure 4A:
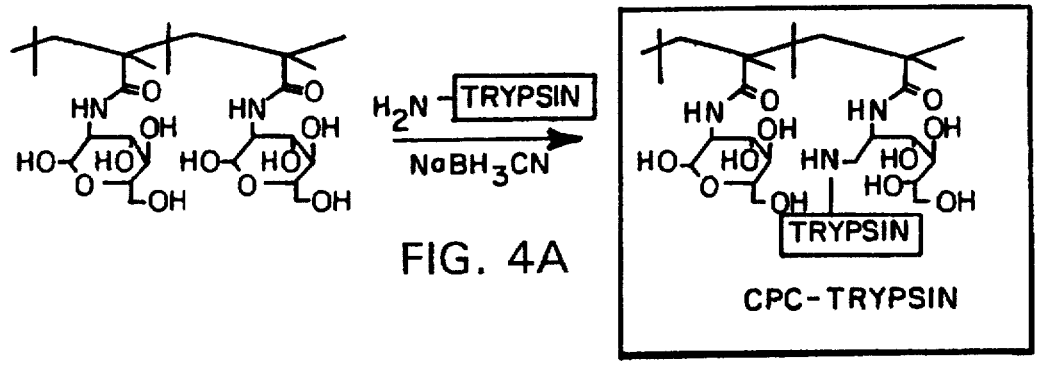
FIG. 4A describes the reaction of trypsin with polymer and FIG. 4B describes the activity of the poly(6-N-methacrylamido-6-deoxy-D-glucose)-chymotrypsin conjugate and native chymotrypsin after six hours at temperatures ranging from 40° to 70° C.
Figure 4B:
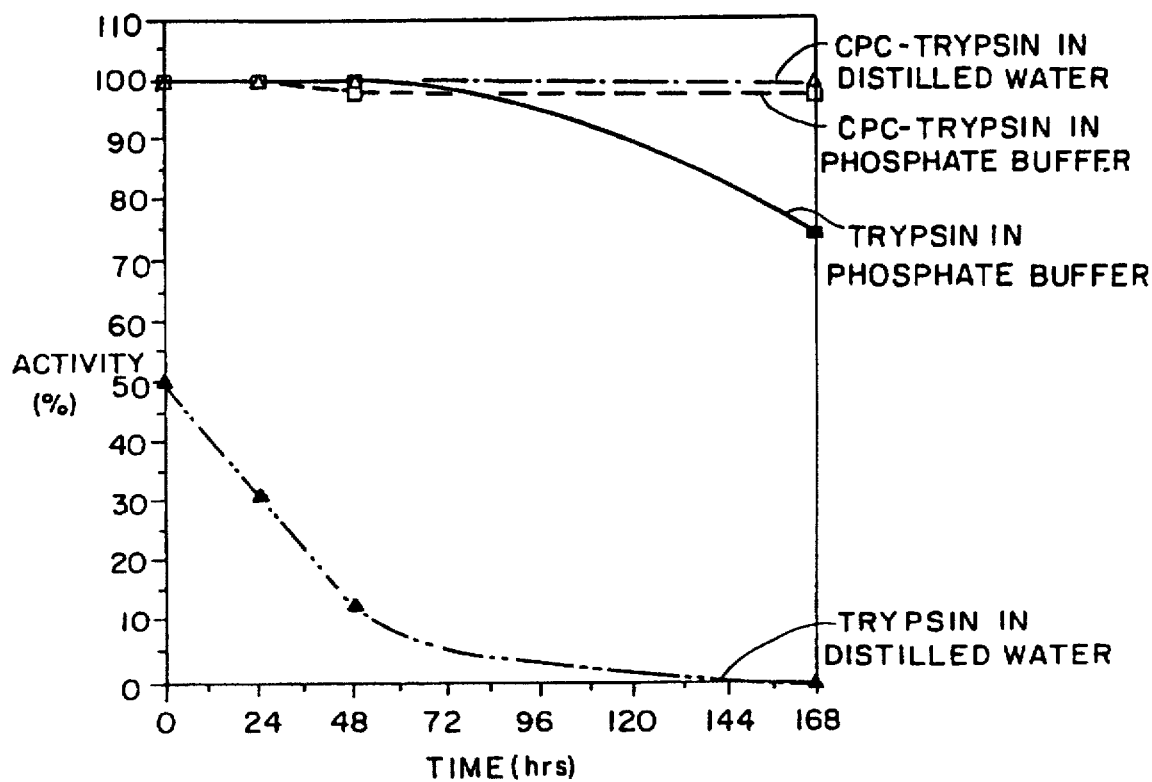

(ii) Stability of the Poly(6-N-methacrylamido-6-deoxy-D-glucose)-α-Chymotrypsin Conjugate The procedure of EXAMPLE 9(a) (i) was repeated in every essential detail except that poly(6-N-methacrylamido-6-deoxy-D-glucose) was used instead of poly(2-N-methacrylamido-2-deoxy-D-glucose). Similar to the findings for the enhanced stability of the poly(2-N-methacrylamido-2-deoxy-D-glucose) α-chymotrypsin conjugate, the poly(6-N-methacrylamido-6-deoxy-D-glucose-α-chymotrypsin conjugate also demonstrates stability at elevated temperatures as shown in FIG. 4.

EXAMPLE 10

Peptide Synthesis using Enzyme-Polymer Conjugates

A series of stabilized soluble proteases were prepared having general utility for the synthesis of peptide bonds denoted by the carbohydrate protein conjugates of proteases (CPC-proteases) following sequence:

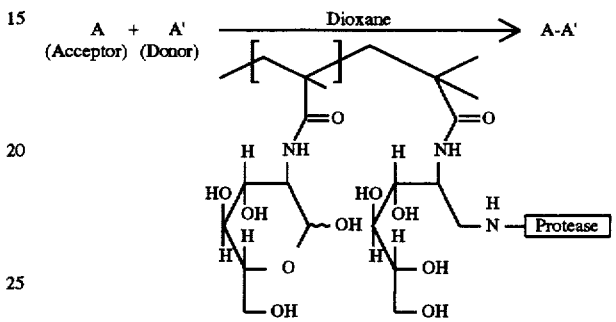

An equimolar solution of AcPhe-OEt (acceptor) and Ala-NH$_2$ (donor) was dissolved in dioxane containing 5 vol % tertiary amine and approximately 1 vol % water at 23° C. The solution was shaken at 25 oscillations/min and approximately 10 units of poly(2-N-methacrylamido-2-deoxy-D-glucose) α-chymotrypsin conjugate was added. The reaction was monitored using HPLC analysis on a C18 column using 25% acetonitrile aqueous solution with 0.1% TFA as the eluent. After 12 hours, HPLC analysis found a quantitative yield of AcPheAla-NH$_2$. The solution was then filtered, the dioxane reduced in vacuo and the product purified by recrystallization obtaining a 97% yield of AcPheAla-NH$_2$. Additional examples of the use of protease-polymer conjugates for the formation of peptide bonds are contained in Table 2. Note that despite the presence of organic solvent, peptide bond formation can be accomplished at elevated temperatures. The use of protease-polymer conjugates for the synthesis of peptide bonds is important, not only for the preparation of peptides and proteins, but also because the chemistry demonstrates the stability of protein-polymer conjugates in organic solvents. Under the same conditions and at the same activity levels used for the preparation of peptide bonds using protease-polymer conjugates, the native enzymes gave less than 5% of the desired product.

TABLE 2

| Enzyme (Solvent, Time) at 23° C. | Acceptor Amino Acid | Donor Amino Acid | Product | Isolated (HPLC) Yield (%) |
|---|---|---|---|---|
| CPC—CT (Dioxane, 12 h) | AcPhe—OEt | Ala—NH$_2$ | AcPheAla—NH$_2$ | 97(100) |
| CPC—CT* (THF, 12 h) | Acphe—OEt | Ala—NH$_2$ | AcPheAla—NH$_2$ | 94(98) |
| CPC—BPN' (Acetonitrile, 22 h) | CbzLeuLeu—OMe | Leu—O$^t$BU | CbzLeuLeuLeu—O$^t$Bu | 68(95) |

TABLE 2-continued

| Enzyme (Solvent, Time) at 23° C. | Acceptor Amino Acid | Donor Amino Acid | Product | Isolated (HPLC) Yield (%) |
|---|---|---|---|---|
| CPC—BPN' (Acetonitrile, 24 h) | CbzLeuLeu—OMe | PheLeu—O$^t$Bu | CbzLeuLeuPheLeu—O$^t$Bu | 92(98) |
| CPC—BPN' (Acetonitrile, 24 h) | CbzValLeu—OMe | PheLeu—O$^t$BU | CbzValLeuPheLeu—O$^t$Bu | 95(98) |
| CPC—BPN' (Acetonitrile, 24 h) | CbzValLeu—OMe | Ala—NH$_2$ | CbzValLeuAla—NH$_2$ | 65(95) |
| CPC—BPN' (Acetonitrile, 24 h) | CbzLeuLeu—OMe | Ala—NH$_2$ | CbzLeuLeuAla—NH$_2$ | 55(90) |
| CPC—T (Acetonitrile, 24 h) | CbzPhe—OH | Leu—OMe | CbzPheLeu—OMe | 65(95) |

*at 50° C.

EXAMPLE 11

Immunoassays using Carbohydrate-Polymer Conjugates

The stabilization of antibodies, as related to storage, elevated temperatures, organic solvent and the like, is highly desirable for their use in diagnostic applications. The stabilization of antibodies for use in an enzyme-linked immunosorbent assay (ELISA) detection of avermectins has been accomplished. The avermectins, which are fermentation products of the soil microorganism *Streptomyces avermitilis*, have potent antiparasitic, insecticidal, and antihelmintic properties. As a result of these properties, the avermectins are finding increasing use in veterinary, medical and agricultural applications. Fisher & Mrozik Macrolide Antibiotics Ch. 14 (1984); Mrozik 25 *J. of Medicinal Chemistry* 658 (1982). Ivermectin (an approximately 80:20 mixture of 22,23-dihydroavermectins B1a and B1b) was succinylated and coupled to a carrier protein, conalbumin, using 1-ethyl-3-(3'-N,N-dimethylaminopropyl)carbodiimide to give Ive-Con. This immunogenic macromolecule was then used to raise a monoclonal antibody, M$_{ab}$ B11C2.1.

The antibody M$_{ab}$ B11C2.1 (0.374 mg) was treated with 2.5 mg of poly(2-N-methacrylamido-2-deoxy-D-glucose and 0.40 mg of sodium cyanoborohydride at 25° C. in 0.05M sodium borate buffer for 12 hours. The antibody-polymer complex (CPC-M$_{ab}$ B11C2.1) was isolated by gel filtration chromatography using 0.05M sodium borate as the eluant on a Superose 12 column. The concentration of M$_{ab}$ B11C2.1 in CPC-M$_{ab}$ B11C2.1 was determined by measurement of its optical density at 280 nm.

The protocol was repeated in every essential detail for the formation of the immunogen-polymer complex (CPC-Ive-Con) except that the ivermectin-conalbumin immunogen was used in place of M$_{ab}$ B11C2.1. The concentration of Ive-Con in CPC-Ive-Con was determined by measurement of its optical density at 280 nm.

Figure 5:
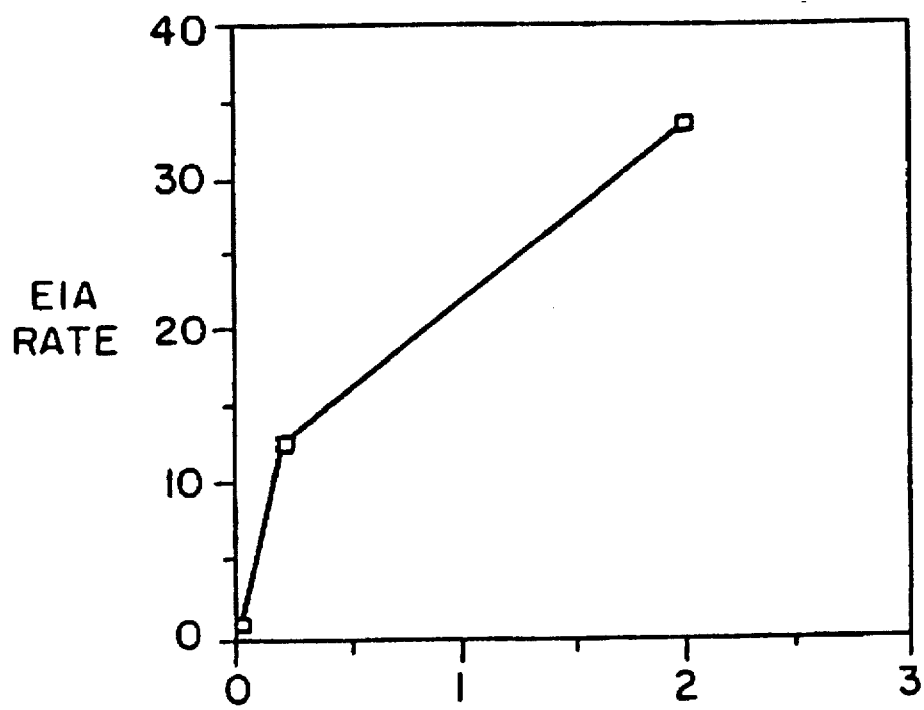
FIG. 5 describes the enzyme immunoassay rate (EIA) of $M_{ab}$ B11C2-1 antibody.
Figure 6:
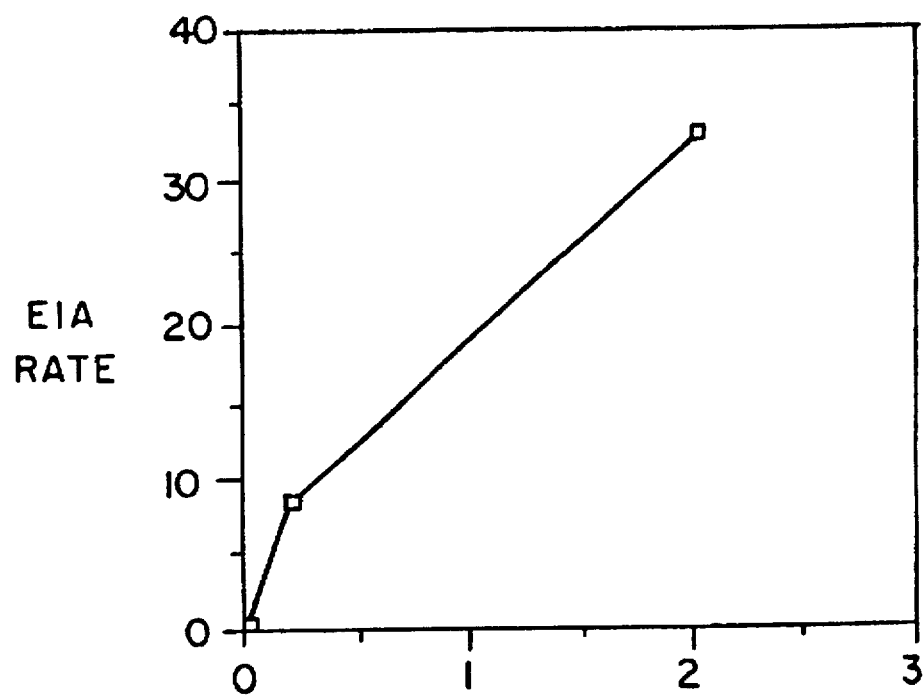
FIG. 6 describes the enzyme immunoassay rate (EIA) of $M_{ab}$ B11C2-1 antibody-poly(2-N-methacrylamido-2-deoxy-D-glucose) conjugate.
Figure 7:
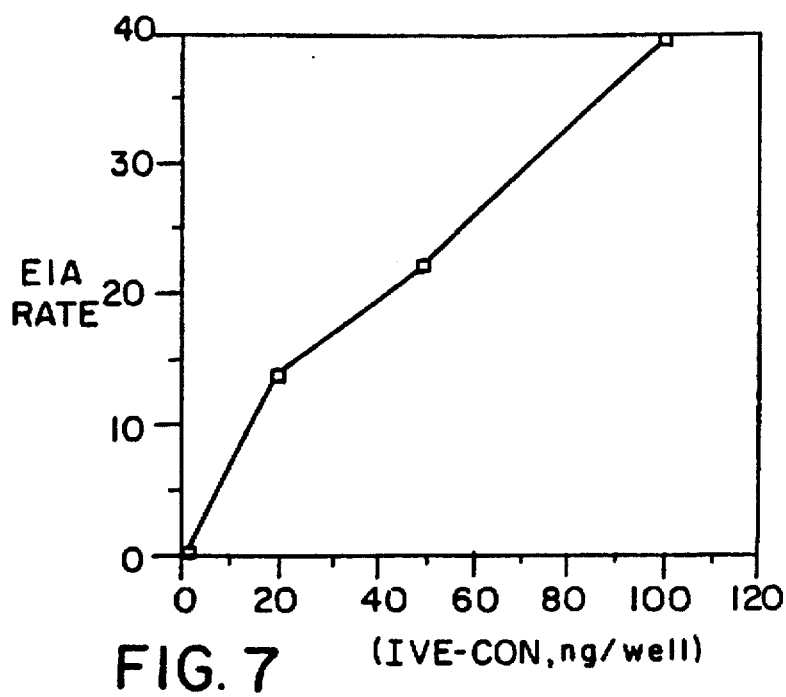
FIG. 7 describes the enzyme immunoassay rate (EIA) on plates coated with Ive-Con antigen-poly(2-N-methacrylamido-2-deoxy-D-glucose) conjugate.
Figure 8:
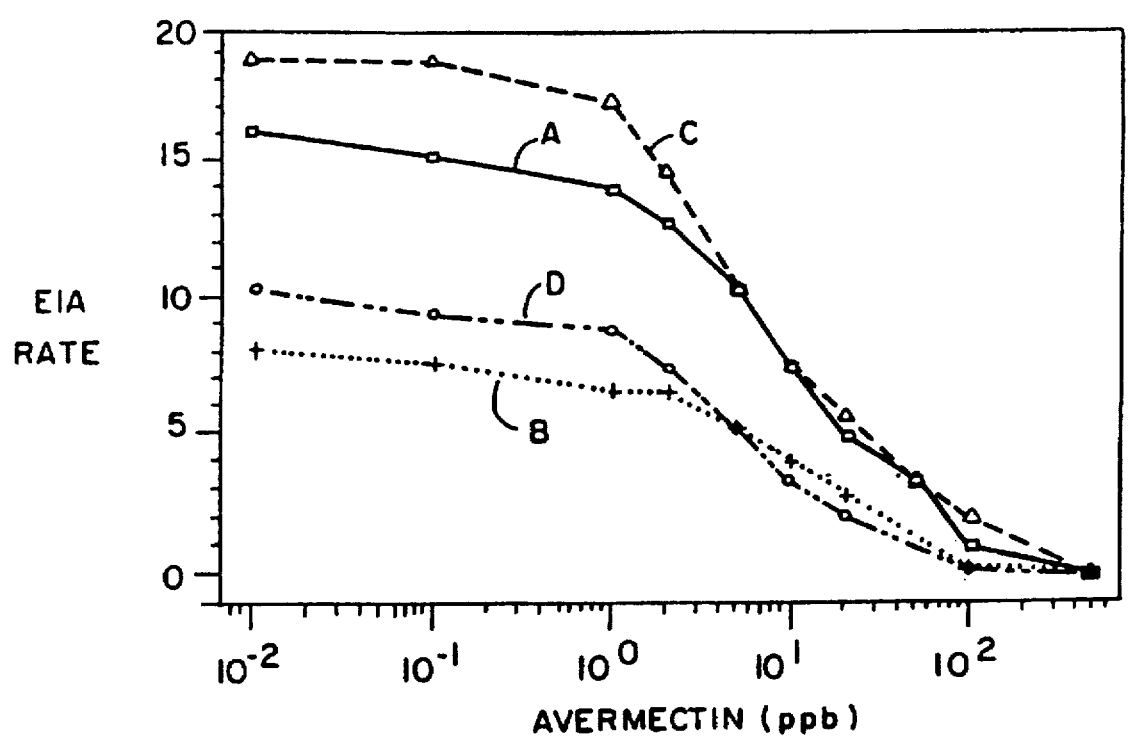
FIG. 8 describes the use of $M_{ab}$ B11C2-1 antibody-polymer conjugate and Ive-Con antigen-poly(2-N-methacrylamido-2-deoxy-D-glucose) conjugate in a competitive assay.

The competency of the protein-polymer conjugates were determined using normal enzyme-linked immunosorbent assay methodology. ELISA plates were coated with 100 ng/well Ive-Con immunogen. The presence of the immunogen was then determined using both M$_{ab}$ B11C2.1 as a control and the protein-polymer conjugate CPC-M$_{ab}$ B11C2.1 (Table 3, FIGS. 5 and 6). These data clearly demonstrate that CPC-$M_{ab}$ B11C2.1 is competent for the detection of the immunogen. The enzyme immunoassay rate (EIA) is equivalent or better than the rate observed using the free antibody.

TABLE 3

Enzyme-linked immunoassay with $M_{ab}$ B11C2.1 and CPC—$M_{ab}$ B11C2.1.

| [$M_{ab}$ B11C2.1] ng/mL | EIA rate | [$M_{ab}$ B11C2.1] in CPC—$M_{ab}$ B11C2.1 ng/mL | EIA rate |
|---|---|---|---|
| 2.00 | 33.8 | 2.00 | 33.3 |
| 0.20 | 12.7 | 0.20 | 8.66 |
| 0.02 | 1.00 | 0.02 | 0.50 |

The immunogen-polymer complex is also competent for the detection of the antibody. Plates were coated with CPC-Ive-Con with concentrations from 1 to 100 ng/well. The presence of the protein-polymer conjugate was then determined using $M_{ab}$ B11C2.1 (Table 4). The data clearly demonstrate that the CPC-Ive-Con protein-polymer conjugate gives significant and easily detectable EIA rates.

TABLE 4

Enzyme-linked immunoassay of plates coated with CPC—Ive—Con.

| [CPC—Ive—Con] ng/well | EIA rate |
|---|---|
| 100 | 39.62 |
| 50 | 22.16 |
| 20 | 13.87 |
| 1 | 0.47 |

The use of these protein-polymer conjugates in a competition assay was also investigated. An ELISA plate with microplate wells was coated with approximately 20 ng/well of Ire-Con immunogen. The competitive binding of $M_{ab}$ B11C2.1 was then measured using an analyte solution of $M_{ab}$ B11C2.1 and ivermectin. Bound $M_{ab}$ B11C2.1 was detected by incubation of the plate with anti-mouse antibody which was conjugated to an enzyme. The presence of the $M_{ab}$ B11C2.1-anti-mouse complex was detected by exposure of the plate with a chromogenic substrate for the enzyme (of the enzyme-anti-mouse conjugate). The sigmoidal dose-response curve is then inversely related to the amount of ivermectin in the competition analyte solution.

The competency of the protein-polymer conjugates was determined by comparison of the response of the control experiment of Ive-Con exposure to $M_{ab}$ B11C2.1 (FIG. 8, curve A) with Ive-Con exposure to CPC-$M_{ab}$ B11C2.1 (FIG. 8, curve B) with CPC-Ive-Con exposure to $M_{ab}$ B11C2.1

(FIG. 8, curve C) and with CPC-Ive-Con exposure to CPC-M$_{ab}$ B11C2.1 (FIG. 8, curve D). The rates at the lowest detectable dose (LDD) and the half-maximal inhibition (I50) for ivermectin in these competition assays are similar for both the control experiment and for the protein-polymer conjugates (Table 5).

TABLE 5

Avermectin hapten inhibition standard curves for Ive—Con and M$_{ab}$ B11C2.1 and their polymer conjugates.

| Coating | Antibody Form | EIA rate at LDD (0.01 ppb) | I$_{50}$ |
|---|---|---|---|
| Ive—Con | M$_{ab}$ B11C2.1 | 15.86 ± 0.20 | 9.03 ± 0.28 |
| Ive—Con | CPC—M$_{ab}$ B11C2.1 | 7.52 ± 0.36 | 6.77 ± 1.70 |
| CPC—Ive—Con | M$_{ab}$ B11C2.1 | 18.79 ± 0.27 | 8.18 ± 1.66 |
| CPC—Ive—Con | CPC—M$_{ab}$ B11C2.1 | 10.49 ± 0.50 | 4.55 ± 0.48 |

CPC = Poly(2-N-methacrylamido-2-deoxy-D-glucose).

These experiments demonstrate that antibody-polymer conjugates can be used for the detection of trace chemicals. These experiments also demonstrate that protein-polymer conjugates are competent in their application for ELISA technology.

The use of protein-polymer conjugates containing both the antibody and enzyme in the same polymer molecule may result in an improvement of the ELISA assay. Enzyme and antibody are conjugated to the polymer as indicated in this Example and in Example 8. The antibody-polymer-enzyme conjugate is used in the competition assay described above. The chromogenic substrate for the enzyme is added after unbound antibody-polymer-enzyme conjugate is washed away. Therefore, use of the antibody-polymer-enzyme in the competition assay eliminates the need to add a second antibody conjugated to an enzyme.

The use of antibody-polymer conjugates in the ELISA assay allows measurements in high concentrations of organic solvent. Therefore, detection of water insoluble chemicals is possible.

EXAMPLE 12

Immunoassays using Polymer Conjugates for Detecting the Presence of Aldrin Pesticide Aldrin is a pesticide used in the agricultural industry. Aldrin contains 95 percent or more of 1,2,3,4,10,10-hexachloro-1,4,4a,5,8,8a-hexahydro-1,4,5,8,-endo, exo-dimethanonaphthalene. Aldrin was succinylated and coupled to a carrier protein using 1-ethyl-3-(3'-N,N, dimethylaminopropyl)carbodiimide to give Con-Aldrin conjugate. This macromolecule was then used to raise a monoclonal antibody, M$_{ab}$ 8H11.

The M$_{ab}$ 8H11 antibody was conjugated to poly (2-N-methacryloyl-2-deoxy-D-glucose), which was made as discussed in Example 5. In this conjugation, the antibodies were conjugated to the polymer using a reductive amination reaction. About 40 mg of polymer and about 20 mg of purified sodium cyanoborohydrate were added to 4 mL of M$_{ab}$ 8H11 (1.5 mg/ml) solution in 0.2M sodium borate and 0.1M sodium chloride at a pH of 8.2. The solution was incubated at 37° C. for 48 hours. The conjugated M$_{ab}$ 8H11 (hereafter CPC-M$_{ab}$ 8H11) was separated from the unreacted antibody by gel filtration in which SEPHACRYL S-300 HR resin was used. The column was eluted with 20 mM sodium phosphate and 50 mM sodium chloride at a pH of 7.0 at a rate of 0.5 mL/min. The conjugated antibody concentration was determined by measuring absorption of the CPC-M$_{ab}$ 8H11 solution at 280 mM and subtracting the contribution of the polymer. The overall yield of the conjugation reaction and purification was about 20%. The purified CPC-M$_{ab}$ 8H11 was concentrated using a membrane filtration apparatus. The purified CPC-M$_{ab}$ 8H11 was lyophilized to give a white powder that could be stored at room temperature without loss of catalytic activity. Lyophilization was done under typical conditions.

The stability of the CPC-M$_{ab}$ 8H11 was studied in a non-ideal environment using a general enzyme-linked immunoassay (EIA). The CPC-M$_{ab}$ 8H11 and M$_{ab}$ 8H11 were exposed to a non-ideal environment and then assayed for their remaining activity in an enzyme immunoassay. After the treatments listed below, in parts a, b and c of this example, to determine the stability, whether thermal or inorganic solvent, the plates were treated with CPC-M$_{ab}$ 8H11 and M$_{ab}$ 8H11, and followed by washing with buffer solution to remove unbound antibodies.

An antimouse-enzyme conjugate was used to detect bound CPC-M$_{ab}$ 8H11 or M$_{ab}$ 8H11 after the treatments in parts a, b and c. A chronogenic substrate for the antimouse-antibody-enzyme conjugate was used to derive the data listed below in Tables 6, and 7 in parts a and c.

a. Thermal Stability of CPC-M$_{ab}$ 8H11 Conjugate

Prior to using immunoassay technique, the native M$_{ab}$ 8H11 (1.6 mg/ml) and 220 µL of the CPC-M$_{ab}$ 8H11 (protein concentration 1.6 µg/mL) were placed in separate micro test tubes with 20 mM sodium phosphate and 50 mM sodium chloride, pH 8.0. The tubes were immersed in a water bath at an elevated temperature. After the incubation time, the solutions were cooled down to room temperature and assayed for the activity that is described above.

Figure 9:
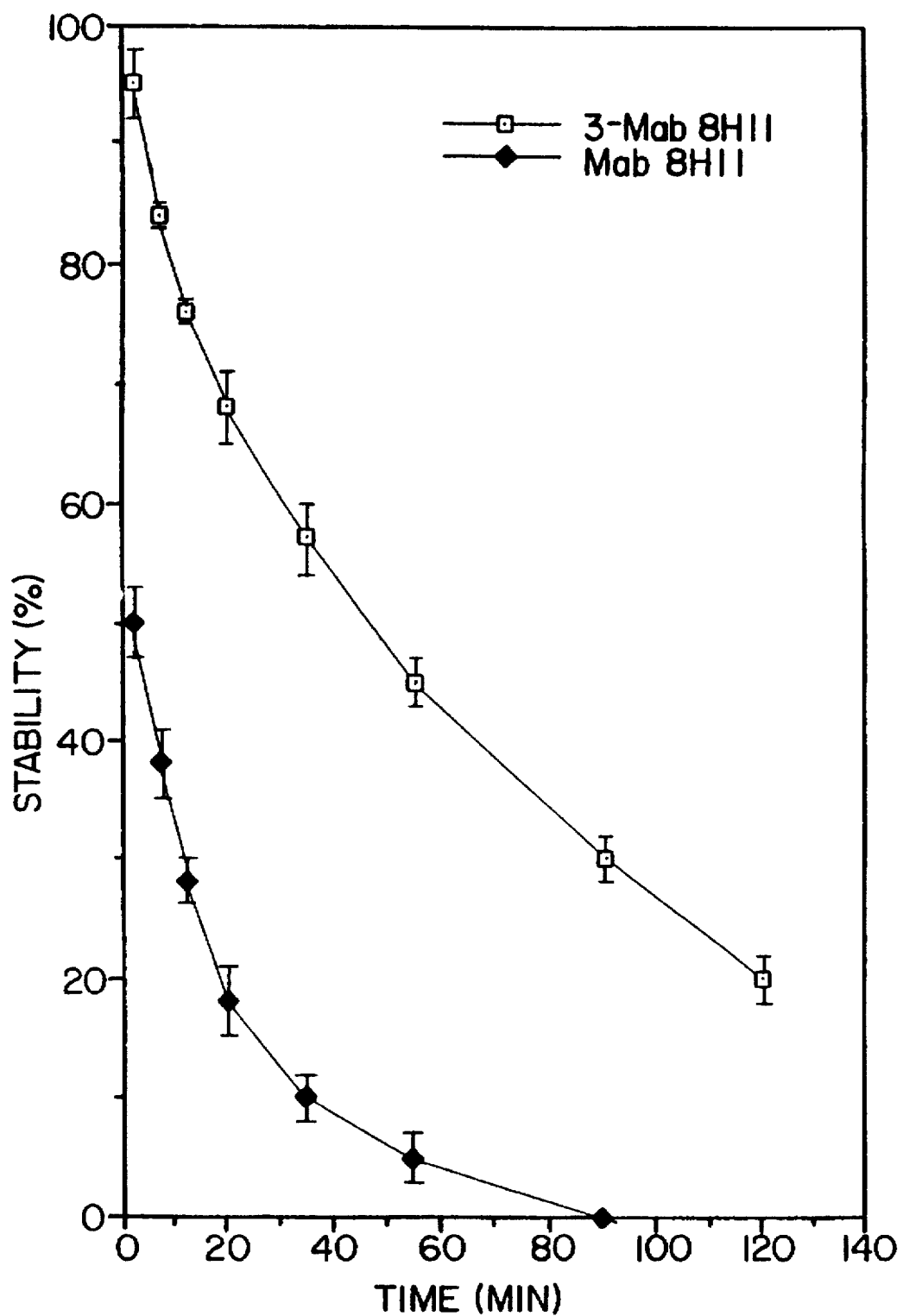
FIG. 9 illustrates the stability over time at 60° C. of the conjugated monoclonal antibody 8H11 as compared to the native monoclonal antibody 8H11.
Figure 10:
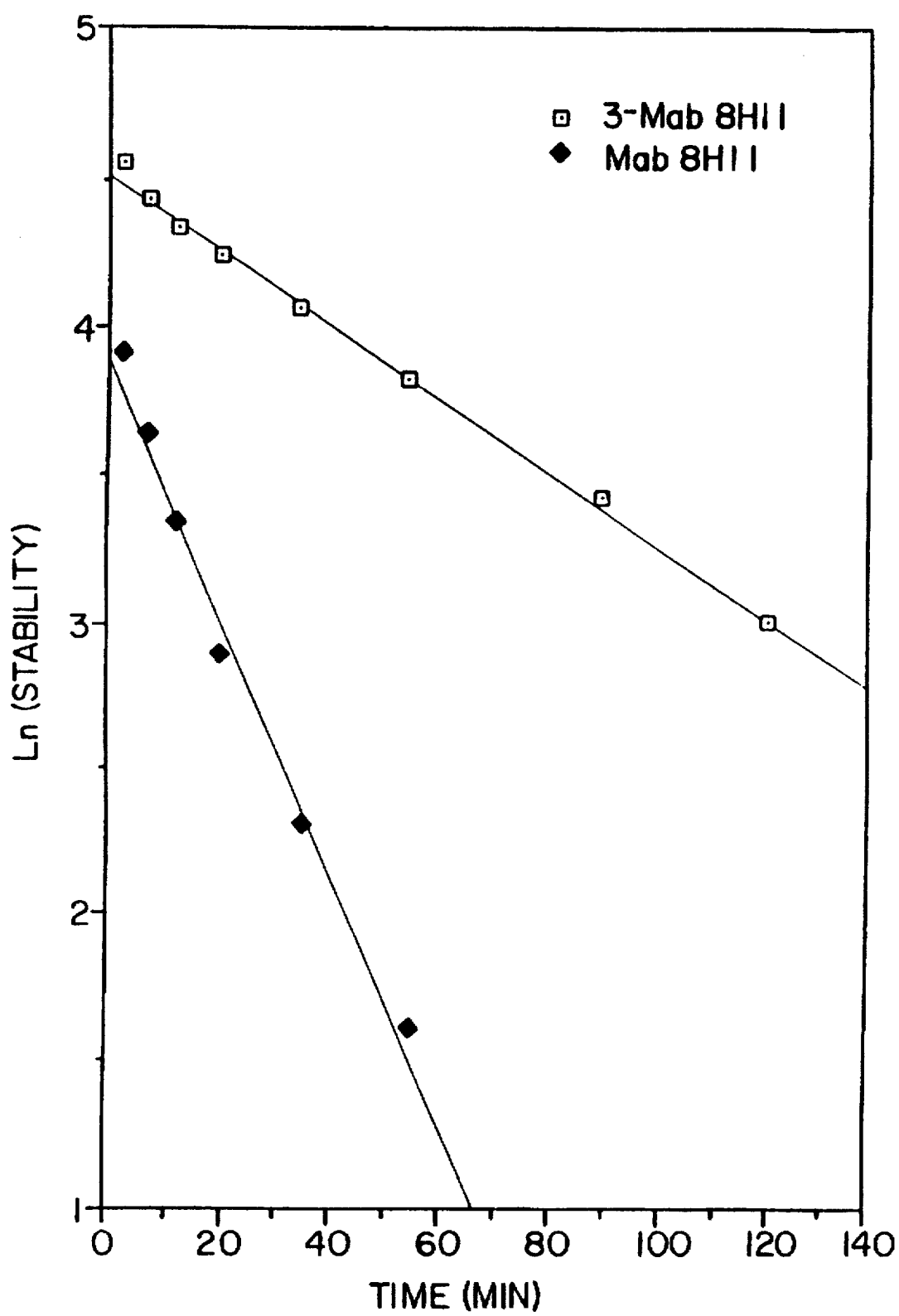
FIG. 10 illustrates that the denaturation of both the conjugated monoclonal antibody 8H11 and native monoclonal antibody 8H1 is a first order kinetic process.

As can be seen from FIG. 9, the CPC-M$_{ab}$ 8H11 is more stable than the native M$_{ab}$ 8H11 over time. At different temperatures, the denatuation of both the CPC-M$_{ab}$ 8H11 and the M$_{ab}$ 8H11 was found to be a first order kinetic process, as can be further seen in FIG. 10.

TABLE 6

Denaturation Constant k$_1$ (min$^{-1}$) of CPC—M$_{ab}$ 8H11 and M$_{ab}$ 8H11) at Different Temperatures

| Temp.(°C.) | CPC—M$_{ab}$ 8H11 | M$_{ab}$ 8H11 | k$_1$(M$_{ab}$)/k$_1$(CPC—M$_{ab}$) |
|---|---|---|---|
| 55 | 1.9 × 10$^{-3}$ | 8.9 × 10$^{-3}$ | 4.7 |
| 60 | 1.2 × 10$^{-2}$ | 4.4 × 10$^{-2}$ | 3.7 |
| 65 | 7.4 × 10$^{-2}$ | 48 × 10$^{-2}$ | 6.5 |

As can be seen in the Table 6, the conjugation process reduced the denaturation rate constants by four to six times.

b. Organic Solvent Stability of CPC-M$_{ab}$ 8H11

Figure 11:
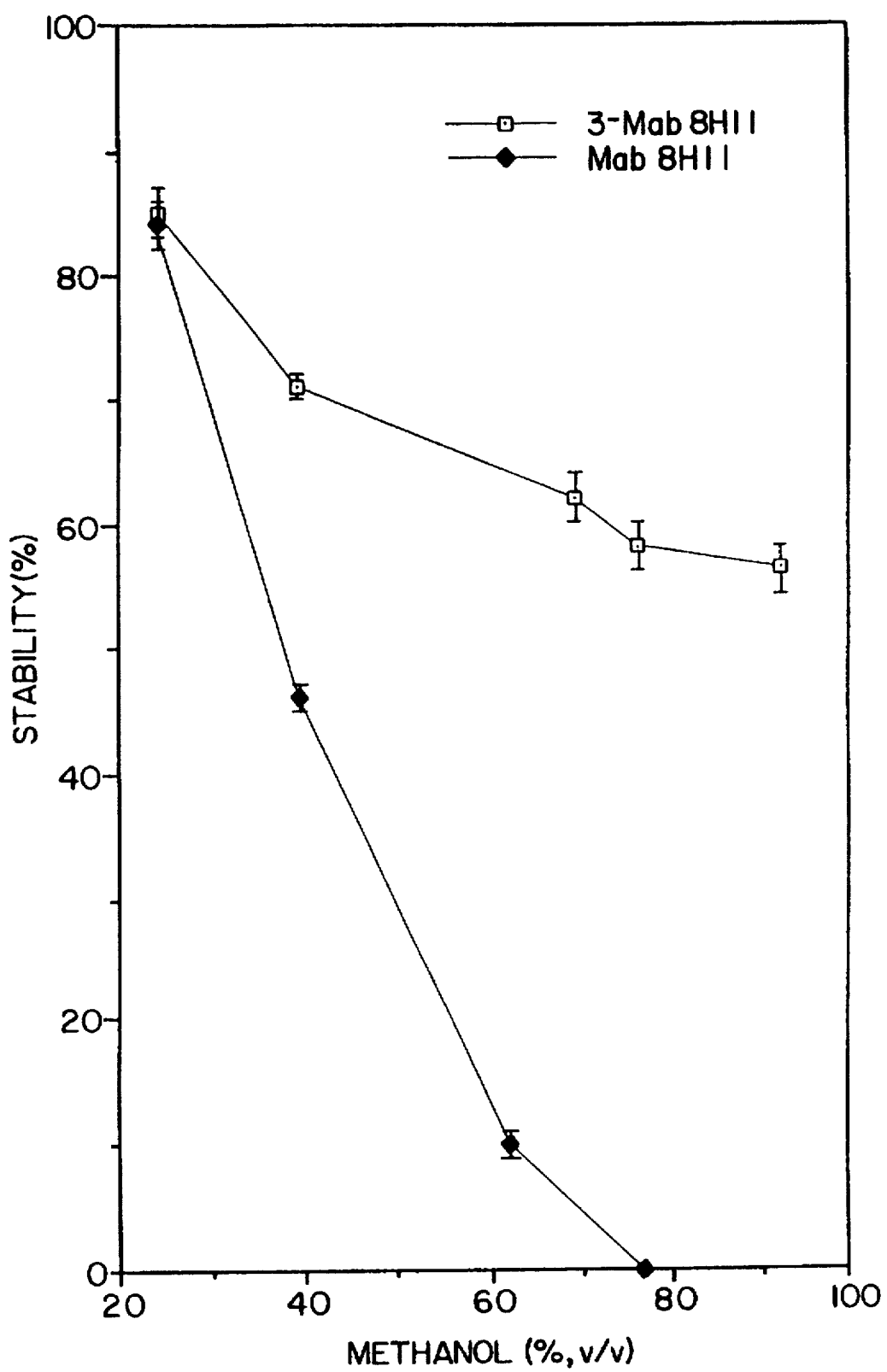
FIG. 11 illustrates the stability of the conjugated monoclonal antibody 8H11 in methanol as compared to the native monoclonal antibody 8H11.

The assay procedure described above to study to the stability of CPC-M$_{ab}$ 8H11 was used in the study of the CPC-M$_{ab}$ 8H11 and organic solvents. The CPC-M$_{ab}$ 8H11 was tested in a number of aqueous organic co-solvents, as can be seen in FIG. 11. The percent stability of the CPC-M$_{ab}$ 8H11 is much greater than native M$_{ab}$ 8H11. The co-solvent used in this test was water-methanol. In the 70% methanol solution, M$_{ab}$ 8H11 lost its activity completely in about five hours. Contrastingly, CPC-M$_{ab}$ 8H11 kept at least half of its activity in up to 95% water-methanol solution. Thus, it can be concluded that the CPC-M$_{ab}$ 8H11 is more stable than M$_{ab}$ 8H11 in a co-solvent of water and methanol.

c. Treatment of Lyophilized Powders of CPC-M$_{ab}$ 8H11 and M$_{ab}$ 8H11

Lyophilized powders of $M_{ab}$ 8H11 and CPC-$M_{ab}$ 8H11 were treated with a number of anhydrous organic solvents, as can be seen in Table 7 below.

TABLE 7

Stability (%) of CPC—$M_{ab}$ 8H11 and $M_{ab}$ 8H11 in Anhydrous Organic Solvents

| Organic Solvents | CPC—$M_{ab}$ 8H11 | $M_{ab}$ 8H11 |
|---|---|---|
| Acetonitrile | 96 | 0 |
| Methanol | 60 | 0 |
| Isopropanol | 57 | 0 |
| Ethyl Acetate | 100 | 70 |
| Hexane | 65 | 69 |

As shown in Table 7 above, the native antibody powder is totally denatured in acetonitrile in about five hours, while the CPC-$M_{ab}$ 8H11 is intact. In methanol, isopropanol and ethyl acetate, CPC-$M_{ab}$ 8H11 also showed higher stability than $M_{ab}$ 8H11.

EXAMPLE 13

Stabilization of Glucose Oxidase

Preparation of Conjugated Glucose Oxidase

A series of stabilized enzymes were prepared, where the enzymes were modified using the poly (2-N-methacrylamido-2-deoxy-D-glucose) of Example 5. The treatment for all of the enzymes was equivalent, except where noted.

The enzymes were conjugated to the polymer. The enzyme of interest was dissolved at 1 mg/mL in 50 mM borate buffer, having a pH of 9.0. Two samples were made, one sample where the enzyme was conjugated to the polymer, and a second sample containing native enzyme. The polymer was added to the first sample in an amount of 10 mg/mL to the conjugation buffer. Both samples, control and conjugated enzyme polymer, were assayed at 25° C. To the polymer sample NaCNBH$_3$ was added at 10 mg/mL and the reaction mixture was incubated at 37° C. for 48 hours. The enzyme activity was monitored periodically. After 48 hours, the activity was measured and the samples were dialyzed against 100 mM phosphate buffer having a pH of 6. The retention of the initial activity was calculated on a volume basis and the samples were tested for altered thermal stability and thermal competence. The $K_m$ values were also obtained for the conjugated and native enzymes.

EXAMPLE 13a

Stability of Enzymes

Glucose Oxidase

In this thermal stability compatible buffer study, three separate trials were completed at various temperatures. In Trial 1, the enzyme was conjugated using borate buffer. In Trial 2, the enzyme was conjugated using phosphate buffer, and in Trial 3 the enzyme was conjugated using cerate buffer, plus D-gluconic acid lactone. In addition, in each trial the effect of the NaCNBH$_3$ with the native enzyme was measured, as was the stability effect of cellobiose and NaCNBH$_3$ with the native enzyme.

In this experiment, to determine the thermal stability, a compatible buffer, 100 mM phosphate buffer having a pH of 6.0, was warmed to the prescribed temperature, as the enzymes were kept on ice. A small amount of enzyme was added to warmed buffer and activity was measured at time intervals. The assay temperature was maintained at 25° C.

Modified Conditions of Trial 3

The one milligram samples of glucose oxidase were dissolved in 1 mL borate buffer (pH 8.5). D-gluconic acid lactose was added at 100 mg/mL to each sample for enzyme protection during treatment. Upon dialysis, native glucose oxidase retained 35% of its initial activity and the conjugated glucose oxidase retained 31% of its initial activity.

Modified Conditions of Trial 2

Phosphate buffer was initially tried as a conjugation buffer (100 mM at pH 8.5). Glucose oxidase was added at 1 mg/mL to phosphate buffer and NaCNBH$_3$ was added. To the native enzyme in 1 mg/mL amount, cellobiose was added at 2 mg/mL along with NaCNBH$_3$ at 10 mg/mL. In another sample, NaCNBH$_3$ was added at 10 mg/mL to 1 mg/mL of native enzyme.

Modified Conditions of Trial 1

Procedures for preparation of conjugated enzyme were followed as described above in the preparation of conjugated glucose oxidase. To the native enzyme in an amount of 1 mg/mL, cellobiose was added at 2 mg/mL along with NaCNBH$_3$ at 10 mg/mL. In another sample, NaCNBH$_3$ was added at 10 mg/mL to 1 mg/mL of native enzyme.

All samples were incubated for i hour at 37° C. Though activity retention through treatment was quite high (native glucose oxidase 88%, conjugated glucose oxidase 75%, NaCNBH$_3$ treated glucose oxidase 96% and cellobiose treated glucose oxidase 102%), no significant difference in t1/2 was observed in the thermal stability study (see Table 8 below).

Thermal Stability of Glucose Oxidase

The thermal stability of glucose oxidase at different temperatures was measured. The mean half-life, measured in minutes, along with the standard deviation (in parentheses) are listed for three completely independent trials. A dash indicates that no data was collected.

TABLE 8

| Temp. | Sample | Trial 1* Min. S.D. | Trial 2** Min. S.D. | Trial 3*** Min. S.D. |
|---|---|---|---|---|
| 50° C. | Control | — | — | 2580 (456) |
|  | Conjugated | — | — | 2274 (132) |
| 60° C. | Control | 78.4 (12.4) | 72.0 (1.6) | 74.8 (4.97) |
|  | Conjugated | 95.3 (9.8) | 70.5 (10.7) | 83.1 (0.13) |
|  | NaCNBH$_3$ | 96.6 (2.1) | 80.7 (1.1) | — |
|  | Cellobiose | 90.0 (8.8) | 65.7 (5.4) | — |
| 70° C. | Control | 4.24 (0.08) | 4.38 (0.34) | 2.44 (0.03) |
|  | Conjugated | 5.41 (0.24) | 4.64 (0.01) | 2.38 (0.01) |
|  | NaCNBH$_3$ | 4.23 (0.04) | 5.26 (0.03) | — |
|  | Cellobiose | 5.13 (1.02) | 4.54 (0.21) | — |
| 80° C. | Control | 0.52 (0.04) | 0.33 (0.01) | 0.32 (0) |
|  | Conjugated | 0.60 (0.01) | 0.36 (0.08) | 0.32 (0) |
|  | NaCNBH$_3$ | 0.52 (0.05) | 0.43 (0.08) | — |
|  | Cellobiose | 0.57 (0.03) | 0.38 (0.01) | — |

*Trial 1 — The enzyme was conjugated using 50 mM borate buffer (pH 9.0).
**Trial 2 — The enzyme was conjugated using 100 mM phosphate buffer (pH 8.5).
***Trial 3 — The enzyme was conjugated using 100 mM borate buffer, pH 8.5 plus 10 mg/mL D-gluconic acid lactone.

As can be seen from Table 8 above, the conjugated enzyme is more heat stable than the native enzyme.

EXAMPLE 13b

Horseradish Peroxidase Treatment

Enzyme was conjugated to the polymer as stated above. The conjugated enzyme was dialysized against phosphate buffer using 300K Da dialysis tubing. After dialysis, 69% of the native enzyme's activity and 78% of the conjugated enzyme's activity was retained (on a volume basis).

Thermal Stability

In the 60° and 70° C. studies, it was observed that the t1/2 of the conjugated enzyme was less than the native enzyme. For example, at 70° C. the t1/2 of the native enzyme was 12.1 minutes, but 4.9 minutes for the conjugated enzyme; and at 60° C. the t1/2 of the native enzyme was 47.7, but 24.9 minutes for the conjugated enzyme.

Thermal Competence

Figure 12A:
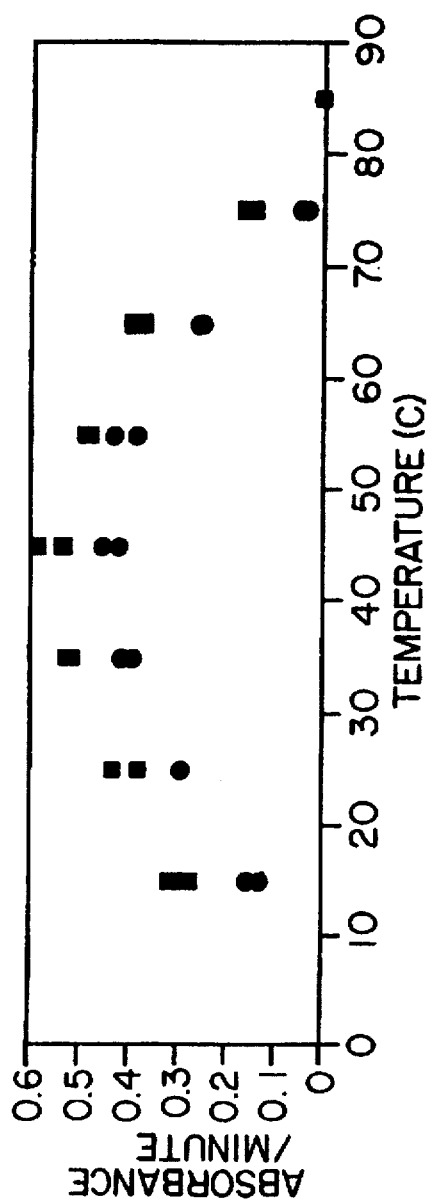
FIG. 12 illustrates the thermo competence of horseradish peroxidase (HRPO). The activity of horseradish peroxidase at different temperatures was measured. Squares represent the activity HRPO which was not conjugated to the polymer. Circles represent the activity of HRPO which was conjugated to the polymer, and dA/dt represents the change in absorbance/minute. In the upper panel (FIG. 12A), the raw data is shown. In the lower panel (FIG. 12B), the activity of the conjugated enzyme was standardized to be identical to the untreated enzyme at 25° C.
Figure 12B:
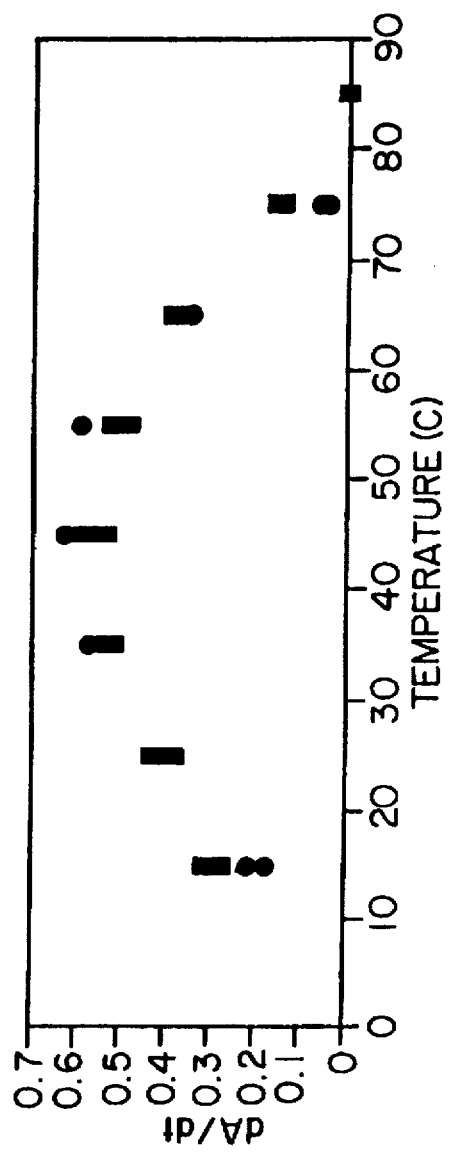

There was no observable difference in thermal competence of the treated enzyme and the untreated enzyme, see FIG. 12.

$K_m$

The $K_m$ was determined as described in Segel *Biochemical Calculations*, 2nd ed., pp 233–241, John Wiley & Sons, New York, which is incorporated herein by reference. The $K_m$ of the conjugated enzyme (0.26 mM) was indistinguishable from the native enzyme (0.23 mM). See FIG. 12.

Thermal competence of HRPO

The activity of horseradish peroxidase at different temperatures was measured. Squares represent the activity HRPO which was not conjugated to the polymer. In FIG. 12, circles represent the activity of HRPO which was conjugated to the polymer, and dA/dt represents the change in absorbance/minute. In the upper panel, the raw data is shown. In the lower panel, the activity of the conjugated enzyme was standardized to be identical to the untreated enzyme at 25° C.

EXAMPLE 13c

Lactic Dehydrogenase

Figure 13A:
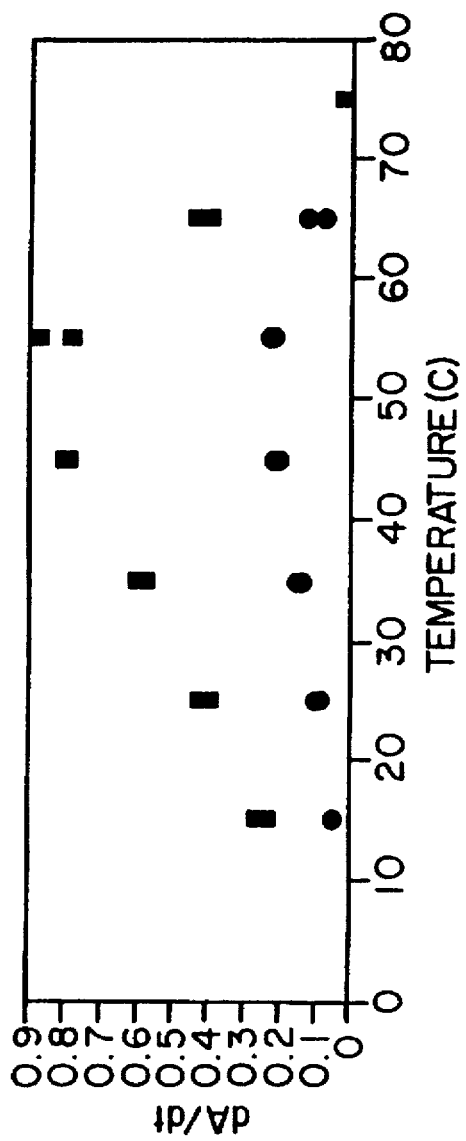
FIG. 13 illustrates the thermo competence of lactic dehydrogenase (LDH). The activity of lactic dehydrogenase at different temperatures was measured. Squares represent the activity of LDH which was not conjugated to the polymer. Circles represent the activity of LDH which was conjugated to the polymer, and dA/dt represents the change in absorbance/minute. In the upper panel (FIG. 13A), the raw data is shown. In the lower panel (FIG. 13B), the activity of the conjugated enzyme was standardized to be identical to the untreated enzyme at 25° C.
Figure 13B:
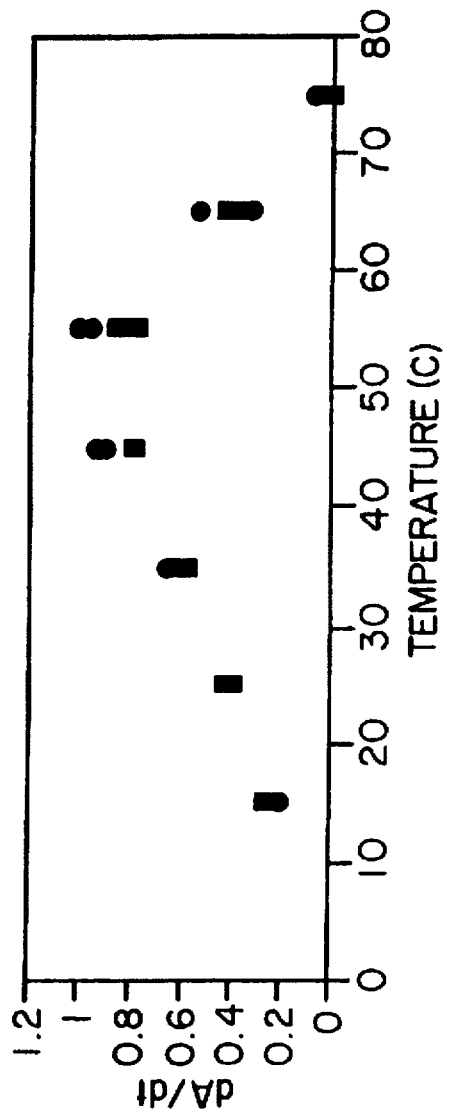

The activity of lactic dehydrogenase was measured. The enzyme was conjugated as described above in Example 11 and compared to the native enzyme. As can be seen in FIG. 13, the conjugated enzyme was more active than the native enzyme at temperatures between about 35° to about 75° C.

EXAMPLE 13d

Pyruvate Kinase

The thermal stability of pyruvate kinase at different temperatures was measured. Mean half-life, measured in minutes, along with the standard deviation (in parentheses) are listed in Trial 1. The enzyme was conjugated using 100 mM borate buffer (pH 8.5).

TABLE 9

| Temp. | Sample | Trial 1 Min. S.D. |
|---|---|---|
| 60° C. | Native | 8.2 (0.83) |
| | Conjugated | 14.0 (0.01) |
| 70° C. | Native | 0.14 (0) |
| | Conjugated | 0.17 (0.03) |
| 80° C. | Native | 0.11 (0) |
| | Conjugated | 0.17 (0.01) |

As can be seen from Table 9 above, the conjugated enzyme was more stable at higher temperatures as compared to the native enzyme.

EXAMPLE 14

Digestion of lambda DNA and PBR322 with conjugated-EcoR1

An endonuclease, EcoR1, was conjugated to poly (2-N-methacryloyl-2-deoxy-D-aminoglucose). The poly(2-N-methacryloyl-2-deoxy-D-aminoglucose) was prepared as in Example 5.

The EcoR1 enzyme conjugate with poly(2-N-methacryloyl-2-deoxy-D-aminoglucose) (300,000 daltons) was prepared by adding purified sodium cyanoborohydride (10 mg, $1.6 \times 10^{-4}$ mol) and (4 mg, $7 \times 10^{-7}$ mol) of poly(2-N-methacryloyl-2-deoxy-D-aminoglucose) in 200 µL of 0.2M sodium borate to a 200 µL solution of EcoR1 (1250 units of activity per µL). The reaction solution was maintained at 37° C. for 6 days.

Gel filtration chromatography was performed using either a BIO RAD 30 cm×0.5 cm Sephacryl S-200 HR economy column with 0.02M sodium tetraborate pH 8.0 as an eluent at 1 mL per minute, or a Pharmacia XK-16 Sephacryl S-200 HR column with 0.02M sodium tetraborate pH 8.0 as an eluent at 1 mL/min. The absorbance was followed at 280 nm.

The above-described procedure was also conducted for selectively cutting the plasmid PBR322 with conjugated-EcoR1.

The digested lambda DNA was placed on a 0.8% BIO RAD ultra pure DNA agarose gel and developed with a Fotodyne minigel apparatus at 80 volts for one hour. Gel electrophoresis was done to determine the cleavage patterns of the lambda DNA treated by the native enzyme and the EcoR1-conjugate.

The digested PBR322 plasmid was placed on a 0.8% BIO RAD ultra pure DNA agarose gel and developed with a Fotodyne minigel apparatus at 80 volts for one hour. Gel electrophoresis was done to determine the cleavage patterns of the PBR322 plasmid treated by C-2 and the EcoR1-conjugate.

In running the gels, the samples were loaded also with a buffer comprising 0.25% bromophenol blue, 0.25% xylene cyanol FF, and 15% Ficol in water. Gels were developed by staining with ethidium bromide (20 µL of a 5 mg/mL solution was diluted to 100 ml). After staining the gels were photographed.

As can be seen in FIG. 14, the cleavage patterns of the lambda DNA digested by the CPC EcoR1 and the native EcoR1 are the same. Thus, it can be concluded that the conjugated EcoR1's activity has not been inhibited by the conjugation to the polymer.

EXAMPLE 15

Digestion of Bovine Serum Albumin with Conjugated-Trypsin

A protease, trypsin, was conjugated to poly(2-N-methacrylamido-2-deoxy-D-glucose). The polymer was prepared as in Example 5. The conjugation was done under the conditions as described in Example 8. The conjugated trypsin was separated from the trypsin that was not conjugated to the polymer using gel filtration chromatography. The gel filtration step was similarly conducted under the conditions described in Example 8.

The conjugated trypsin in an amount of about 2.7 mg/mL, 795 units/mL was mixed with bovine serum albumin (BSA) in an amount of about 50 mg/mL at 30° C. for 48 hours. Another mixture, Control-1 containing BSA in an amount of about 50 mg/mL in 100 mM Tris-HCL buffer pH 8.6 was prepared and combined with native trypsin in an amount of 0.05 mg/mL, 795 units/mL. Control-1 mixture was incubated at 30° C. for 48 hours.

After digestion, a SDS-PAGE (sodium dodecyl sulfate polyacrylamide gel electrophoresis) was performed. A Pharmacia Phast System with PhastGelhomgeneous 20 SDS- PAGE was used. The gel was stained with ethidium bromide. After staining, the gel was photographed.

As can be seen from FIG. 16, the digestion of the BSA by the conjugated-trypsin and the native trypsin was the same. In FIG. 16, note that lanes 3 through 5 are molecular weight markers (66000, 45000, 36000, 29000, 24000, 20100 daltons).

EXAMPLE 16

Hydrogel Formation Reaction with α-deoxy-2-N-methacrylamido-D-glucose

To a 0.5 mL of water, previously triply distilled and freeze-thaw-degassed for three cycles, was added 9 mg of ammonium persulfate and the solution was cooled to 1° C. To this solution was then added 0.84 g of 2-deoxy-2-N-methacrylamido-D-glucose, as prepared in Example 5, dissolved in 3.5 mL of water dropwise. The mixture was stirred for 2 hours, at which the stirbar does not stir the gelling solution efficiently. By 18 hours the reaction solution is completely gelled as a colorless, transparent gel containing 83% water.

The above procedures were followed for the Trials 1–7 in Table 10, with Trial i being the above-described procedure, with the exceptions noted in Table 7.

TABLE 10

Hydrogel Formation Reactions

| Trials | $H_2O^a$ (mL, %$^b$) | $(NH_4)_2S_2O_8$ (g, $M$) | Monomer (g, m$M$) | Temperature (°C.) |
|---|---|---|---|---|
| 1 | 3.57 or 4, 80 | 0.0090, 0.01 | 0.84, 0.85 | 0$^d$ |
| 2 | 5, 83 | 0.0181, 0.02 | 1.00, 0.81 | RT |
| 3 | 4.5, 82 | 0.0090, 0.01 | 1.00, 0.90 | RT |
| 4 | 4, 80 | 0.0089, 0.01 | 1.00, 1.01 | 5$^c$ |
| 5 | 8, 89 | 0.0094, 0.005 | 1.00, 0.51 | 5 |
| 6 | 40, 89 | 0.4909, 0.054 | 5.00, 0.51 | 19.7 |
| 7 | 4, 80 | 0.0091, 0.01 | 0.997, 1.01 | RT |

$^a$Triply glass distilled $H_2O$ was glass distilled once more before use.
$^b$Percentage of water present in gel. Calculated as [(Weight Wet − Weight Dry)/Weight Wet] × 100.
$^c$Reaction was at this temperature for 2–3 hours then was allowed to warm to room temperature for overnight.
$^d$Reaction was at this temperature for 2.5 hours then was allowed to warm to room temperature for overnight.

EXAMPLE 17

Polymerization of Conjugated Enzyme

Part a. Preparation of 2-deoxy-2-N-methacrylamido-D-glucose conjugate of α-chymotrypsin In a 100 mL round-bottomed flask containing 60 mL of 0.2M sodium borate buffer, pH 8, was added 60 mg (2.4× $10^{-6}$ mol) α-chymotrypsin and 90 mg (3.6×$10^{-4}$ mol) of 2-deoxy-2-N-methacrylamido-D-glucose. Upon adding 300 mg (4.8×$10^{-3}$ mol) of sodium cyanoborohydride, the solution was shaken in a constant temperature bath at 35° C. for 48 hours. The conjugate was isolated by HPLC (Sephacryl S-200) using 0.05M sodium borate buffer (pH 8). The solution was then dialyzed against distilled water using a Spectra Por 7 10K MWCO membrane. The solution was lyophilized to give a fluffy white powder with 28% of the original activity.

Part b. Copolymerization of the 2-deoxy-2-N-methacrylamido-D-glucose conjugate of α-chymotrypsin and 2-deoxy-2-N-methacrylamido-D-glucose In a 100 mL round-bottomed flask containing 40 mL of triply distilled, freeze-thaw-degassed water under an atmosphere of nitrogen, was added 1.0 g (4.1×$10^{-3}$ mol) of 2-deoxy-2-N-methacrylamido-D-glucose and 50 mg (2.0× $10^{-6}$) of the 2-deoxy-2-N-methacrylamido-D-glucose conjugate of α-chymotrypsin. To this solution was then added 10 mg (4.4×$10^{-3}$ mol) of ammonium persulfate and the solution was shaken gently at 25° C. for 12 hours. The solution was then dialyzed against distilled water using a Spectra Por 7 LOOK MWCO membrane and then lyophilized to give 1.0 g (95% yield) as a white, fluffy solid.

EXAMPLE 18

Lactone Polymer system

Preparation of poly(2-methacrylamido-2-deoxy-D-gluconolactone)

In a 100 mL round-bottomed flask was added 50 mL of pH 6 phosphate buffer followed by 0.5 mL of bromine. To this solution was added 0.1 g of poly(2-methacrylamido-2-deoxy-D-glucose) and the solution was stirred at 20° C. for 25 min. At this point, a 2.5 wt % solution of sodium thiosulfate was added until the solution became colorless. The solution was then dialyzed against water and the solution was lyophilized to give a 30% yield of poly(2-methacrylamido-2-deoxy-D-gluconolactone).

EXAMPLE 19

Preparation of Disaccharide Polymer System

Part a. Preparation of 1,2,3,4-tetra-O-acetyl-6-O-(2,3,4-tri-O-acetyl-6-deoxy-6-trifluoroacetamido-β-D-glucopyranosyl)-β-D-glucopyranose 1,2,2,3-tetra-O-acetyl-β-D-glucopyranose (1.1 g, 3.2 mmol), silver oxide (0.9 g, 3.9 mmol) and drierite (2.5 g) was placed in a 25 mL, three-necked, round-bottomed flask equipped with a magnetic stirrer, dropping funnel and under an atmosphere of argon. Chloroform (5 mL), (alcohol free), was added and the mixture was stirred for 1 hour protected from light. Iodine (0.2 g) was then added as a catalyst. 2,3,4-tri-O-acetyl-6-deoxy-6-(trifluoroacetamido)-α-D-glucopyranose bromide (1.7 g, 3.6 mmol) dissolved in alcohol-free chloroform (6 mL) was added to the stirred mixture over a period of about 1 hour. After 16 hours, the reaction mixture was filtered through celite and the solvent removed in vacuo. The white crystalline residue was dissolved in hot absolute ethanol to which distilled water was added to the point of cloudiness. Cooling at 0° C. gave a white solid which after filtration and recrystallization from hexane/ether gave a 43% yield of the desired disaccharide.

Part b. Preparation of 6-O-(6-amino-6-deoxy-β-D-glucopyranosyl)-β-D-glucopyranose Dry ammonia was passed into a solution of 5×$10^{-3}$N sodium methoxide in 35 mL of methanol cooled in an ice-salt bath over a 45 minute period. 1,2,3,4-tetra-O-acetyl-6-O-(2,3,4-tri-O-acetyl-6-deoxy-6-trifluoroacetamido-β-D-glucopyranosyl)-β-D-glucopyranose (50 mg, 0.07 mmol) was added to the solution and stirred at 0° C. for 1 hour. Afterwards, Amberlite IR120H$^+$ was added until the solution was neutral, then filtered and the solution was then concentrated under reduced pressure to give a thick oil. Addition of ether/hexane (4:1) and concentration in vacuo yielded, after filtration, a white solid of the desired disaccharide in 78% yield.

What is claimed is:

1. In an immunoassay method of detection wherein the immunoassay method comprises contacting an antibody polymer conjugate with an antigen so as to bind the antigen, and measuring the amount of antigen bound to the antibody polymer conjugate, the improvement wherein the antibody polymer conjugate comprises antibody covalently bonded to a polymer by linker groups, wherein the polymer is selected from the group consisting of a polyvinyl polymer, a polyester polymer, a polyamide polymer and mixtures thereof, the polymer having a main chain molecular weight of at least 5,000, and wherein three or more linker groups covalently bond both the antibody and polymer and said linker groups have at least three hydroxyl groups and not more than 60 carbon atoms, each of said linker groups being selected from the group consisting of

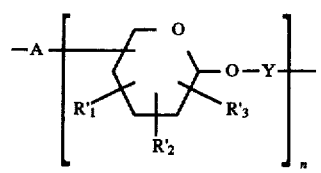

Ia

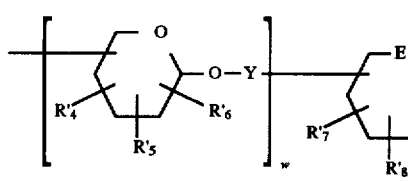

Ib

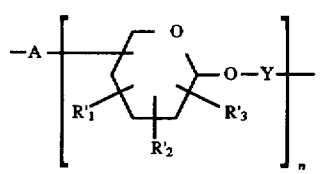

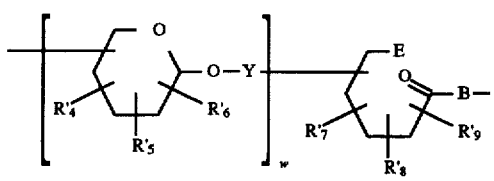

Ic

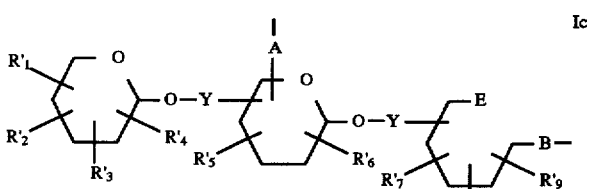

Id

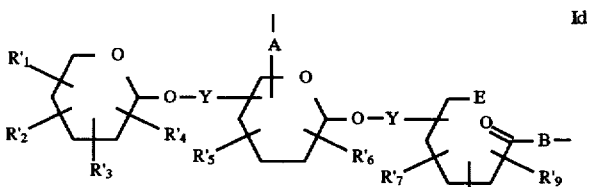

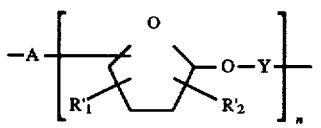

IIa

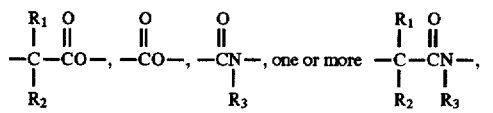

IIb

IIc and

IId wherein

E=—OH or —SH;

n=0 or 1;

W=0 or 1; and

Y=bond or —CH$_2$;

wherein A is bonded to the polymer and is selected from the group consisting of

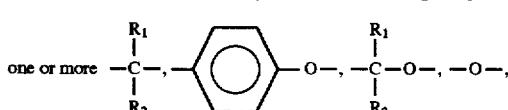

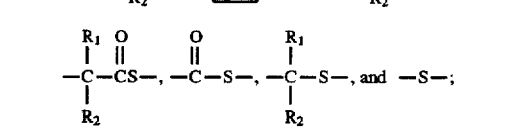

B is bonded to the antibody and is selected from the group consisting of

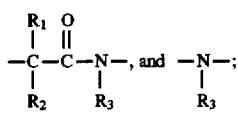

wherein R₁ and R₂ are each selected from the group consisting of H, OH, acetoxy, alkoxy, phenylene, straight chain alkyl or branched chain alkyl having 1 to 12 carbons,

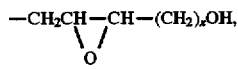

wherein x=2 to 7,

2-hydroxy ethyl, 3-chloro-2-hydroxypropyl, 2-hydroxy-1-methylethyl, 2-hydroxypropyl, 3-hydroxypropyl, 2, 3-dihydroxypropyl, 2 hydroxybutyl, 4 -hydroxybutyl, diethylene-glycol, 5-hydroxypentryl, 6-hydroxyhexyl, triethyleneglycol, 7-hydroxyheptyl, 3,4-dihydroxybutyl, 5-hydroxypentyl, 6-hydroxyhexyl, 2,3-dimethyl-3-hydroxybutyl, 5,6-dihydroxyhexyl, 7-hydroxyheptyl, a residue of a mono-, di-, and trisaccharide;

wherein R₃ selected from the group consisting of H, straight chain alkyl or branched chain alkyl having 1 to 12 carbons,

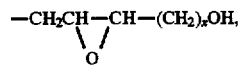

wherein x=2 to 7,

2-hydroxy ethyl, 3-chloro-2-hydroxypropyl, 2-hydroxy-1-methylethyl, 2-hydroxypropyl, 3-hydroxypropyl, 2, 3-dihydroxypropyl, 2 hydroxybutyl, 4-hydroxybutyl, diethylene-glycol, 5-hydroxypentryl, 6-hydroxyhexyl, triethyleneglycol, 7-hydroxyheptyl, 3,4-dihydroxybutyl, 5-hydroxypentyl, 6-hydroxyhexyl, 2,3-dimethyl-3-hydroxybutyl, 5,6-dihydroxyhexyl, 7-hydroxyheptyl, a residue of a mono-, di-, and trisaccharide; and R'₁, R'₂, R'₃, R'₄, R'₅, R'₆, R'₇, R'₈, and R'₉ each selected from the group consisting of H, OH, acetoxy, alkoxy, halogen and phosphate, straight chain alkyl or branched chain alkyl having 1 to 12 carbons,

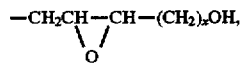

wherein x=2 to 7,

2-hydroxy ethyl, 3-chloro-2-hydroxypropyl, 2-hydroxy-1-methylethyl, 2-hydroxypropyl, 3-hydroxypropyl, 2,3-dihydroxypropyl, 2 hydroxybutyl, 4-hydroxybutyl, diethylene-glycol, 5-hydroxypentryl, 6-hydroxyhexyl, triethyleneglycol, 7-hydroxyheptyl, 3,4-dihydroxybutyl, 5-hydroxypentyl, 6-hydroxyhexyl, 2,3-dimethyl-3-hydroxybutyl, 5,6-dihydroxyhexyl, 7-hydroxyheptyl, a residue of a mono-, di-, and trisaccharide.

2. The method of claim 1, wherein R'₁, R'₂, R'₃, R'₄, R'₅, R'₆, R'₇, R'₈, and R'₉ are selected from the group consisting of H, OH and an alkyl having from 1 to 4 carbon atoms wherein each of the linker groups is a residue of a saccharide selected from the group consisting of a monosaccharide, disaccharide and trisaccharide.

3. The method of claim 1, wherein the antibody is bonded to each of the linker groups through the residue of a lysine group.

4. The method of claim 1, wherein the R'₁ through R'₉ are H or OH and the bond between the antibody and each of the linker groups is a residue of a lysine group on the protein.

5. The method of claim 1, wherein the R'₁ through R'₉ are H or OH and the bond between the antibody and each of the linker groups is a residue of an arginine group on the protein.

6. The method of claim 1, wherein each of the linker groups is

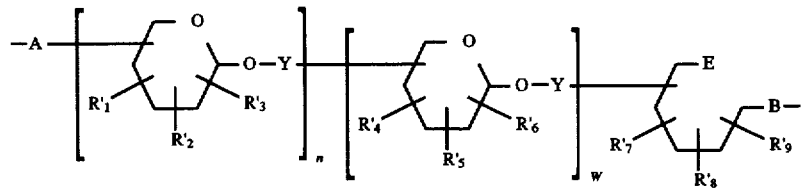

7. The method of claim 1, wherein each of the linker groups is

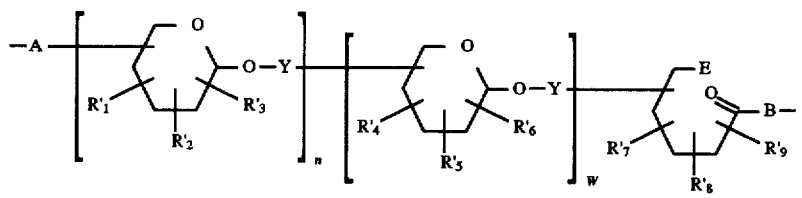
Ib

8. The method of claim 1, wherein each of the linker groups is

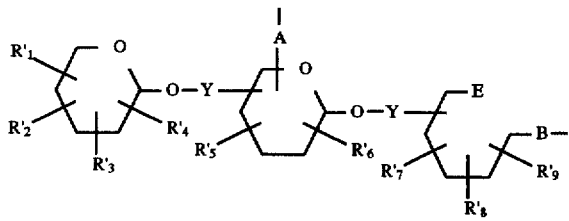
Ic

9. The method of claim 1, wherein each of the linker groups is

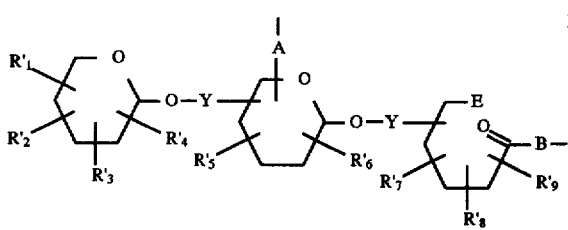
Id

10. The method of claim 1, wherein each of the linker groups is

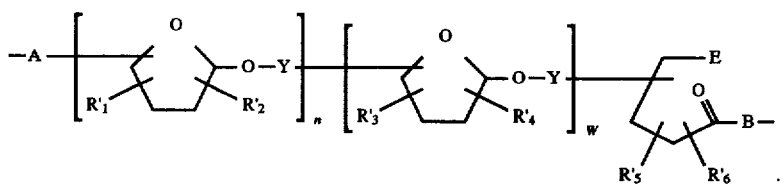
IIa

11. The method of claim 1, wherein each of the linker groups is

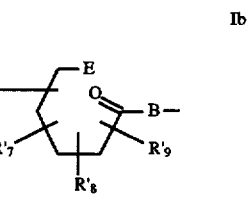
IIb

12. The method of claim 1, wherein each of the linker groups is

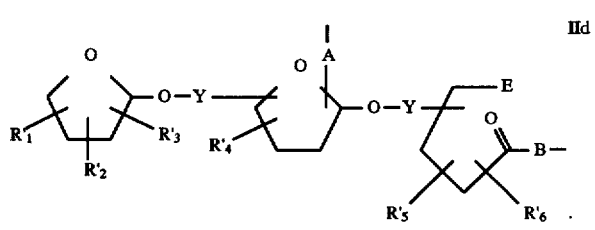
IIc

13. The method of claim 1, wherein each of the linker groups is

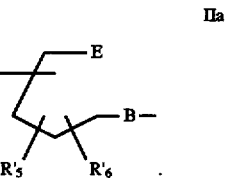
IId

14. The method of claim 1, wherein each of the linker groups is a residue of the monosaccharide selected from the group consisting of 6-amino-6-deoxy-D-glucose, 2-amino-2-deoxy-D-glucose, 3-amino-3-deoxy-D-glucose and mixtures thereof.

15. The method of claim 1, wherein each of the linker groups is a residue of 6-amino-6-deoxy-D-glucose.

16. The method as recited in claim 1 wherein the antibody incorporated into the antibody polymer conjugate has a half life of at least about 110% of the half life of a native antibody in a hostile environment.